United States Patent
Oki

(10) Patent No.: US 8,056,395 B2
(45) Date of Patent: Nov. 15, 2011

(54) METHOD FOR DETECTING A CHEMICAL SUBSTANCE

(75) Inventor: Akio Oki, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/957,890

(22) Filed: Dec. 1, 2010

(65) Prior Publication Data
US 2011/0072887 A1    Mar. 31, 2011

Related U.S. Application Data

(63) Continuation of application No. PCT/JP2010/003358, filed on May 19, 2010.

(30) Foreign Application Priority Data

Jun. 2, 2009   (JP) ................ 2009-132814

(51) Int. Cl.
   *G01N 27/70*   (2006.01)
(52) U.S. Cl. ....... 73/31.07; 73/23.3; 73/31.02; 73/31.03
(58) Field of Classification Search ............... 73/23.3, 73/31.02, 31.03, 31.07, 863.12
   See application file for complete search history.

(56) References Cited

U.S. PATENT DOCUMENTS

| | | | |
|---|---|---|---|
| 3,827,217 A | 8/1974 | Volsy | |
| 6,508,861 B1 * | 1/2003 | Ray | .................. 95/79 |
| 2007/0173731 A1 | 7/2007 | Meka et al. | |
| 2008/0295687 A1 | 12/2008 | Galbrun et al. | |
| 2009/0275852 A1 | 11/2009 | Oki et al. | |

FOREIGN PATENT DOCUMENTS

| | | |
|---|---|---|
| JP | 48-075094 | 10/1973 |
| JP | 2000-504114 | 4/2000 |
| JP | 2002-511792 | 4/2002 |
| JP | 2008-128955 | 6/2008 |
| JP | 2009-502457 | 1/2009 |

(Continued)

OTHER PUBLICATIONS

Phillips, M. et al., "Volatile organic compounds in breath as markers of lung cancer: a cross sectional study", The Lancet, Jun. 5, 1999, pp. 1930-1933, vol. 353.

(Continued)

*Primary Examiner* — Hezron E Williams
*Assistant Examiner* — Paul West
(74) *Attorney, Agent, or Firm* — McDermott Will & Emery LLP

(57) ABSTRACT

The present invention provides a method for detecting easily and efficiently a chemical substance contained in a gas sample at an ultralow amount.
The present invention is directed to detecting method of a chemical substance contained in a gas sample, using an analyzing device with electrostatic atomizer. The analyzing device comprises a vessel, a inlet, a cooling part, an atomizing electrode, a counter electrode, an intermediate electrode, a liquid detecting part, and a detecting electrode. According to a detecting method of the present invention, the gas sample is condensed as a first condensate liquid at the surface of the atomizing electrode. The first condensate liquid is configured to be electric-charged fine particles to obtain a second condensate liquid at the surface of the counter electrode. The resulted second condensate liquid is brought in contact with the detecting electrode and a current voltage is applied between the counter electrode and the detecting electrode. The chemical substance is detected on the basis of the generated current value.

5 Claims, 18 Drawing Sheets

FOREIGN PATENT DOCUMENTS

| WO | WO 97/28446 | 8/1997 |
|---|---|---|
| WO | WO 98/58745 | 12/1998 |
| WO | WO 2009/057256 A1 | 5/2009 |

OTHER PUBLICATIONS

Phillips, M., et al., "Method for the Collection and Assay of Volatile Organic Compounds in Breath", Analytical Biochemistry, 1997, pp. 272-278, vol. 247, Academic Press.

Phillips, M. et al., "Prediction of Heart Transplant Rejection With a Breath Test for Markers of Oxidative Stress", The American Journal of Cardiology, Dec. 15, 2004, pp. 1593-1594.

Moser, B., et al., "Mass spectrometric profile of exhaled breath—field study by PTR-MS", Respiratory Physiology & Neurobiology, 2005, pp. 295-300, vol. 145.

* cited by examiner (A)

(B)

(A)

(B)

(A)

(B)

(A)

(B)

(A)

(B)

(A)

(B)

(A)

(B)

METHOD FOR DETECTING A CHEMICAL SUBSTANCE

This Application is a continuation of International Application No. PCT/JP2010/003358, whose international filing date is May 19, 2010 which in turn claims the benefit of Japanese Patent Application No. 2009-132814, filed on Jun. 2, 2009, the disclosures of which Applications are incorporated by reference herein. The benefit of the filing and priority dates of the International and Japanese Applications is respectfully requested.

TECHNICAL FIELD

The present invention relates to a method for detecting a chemical substance contained in a gas sample.

BACKGROUND ART

Recently, a technique to diagnose illness at an early stage has been established by collecting noninvasively a sample from a living body and analyzing a chemical substance contained in the sample at an ultralow amount. The sample collected from the living body includes urine, exhalation, gas diffused from a skin surface, perspiration, or spit.

For example, Patent Document 1 discloses a method for screening bladder cancer from the amount of hyaluronic acid and hyaluronidase contained in urine. According to the Patent Document 1, a patient disease by bladder cancer has a higher amount of hyaluronic acid in his/her urine than a normal individual. Bladder cancer can be inspected easily and non-invasively with the method disclosed in the Patent Document 1.

Exhalation is also one of important sample for diagnose illness. Not only water, nitrogen, oxygen and carbon dioxide but also metabolic component is contained in the exhalation at an extremely small amount. The metabolic component includes volatile organic compound or volatile sulfide compound released by gaseous exchange between alveoli and blood capillaries. An example of the metabolic component is alcohol, ketone, aldehyde, amine, aromatic hydrocarbon, fatty acid, isoprene, mercaptan, or derivatives from these components.

It is believed that there are some sort of relationship between illness and an ultralow amount of the metabolic component in the exhalation. Non-patent documents 1 to 4 disclose the research revealing correlation between illness and the metabolic component in the exhalation.

Unlike blood, urine or exhalation can be collected without physical and mental pain to a patient. Accordingly, a method for diagnosing with the sample composed of urine or exhalation is expected to be used for domestic diagnosis, follow-up after surgery, or prevention of illness.

However, since urine and exhalation are collected noninvasively, it is known that the concentration of the chemical substance contained in the urine or exhalation, which is suspected to have relationship with illness, is lower than the concentration of the diagnostic marker in a blood. The Patent Document 1 and Non-patent document 4 disclose that urine contains a diagnostic marker at a concentration of only 1 ng/ml and that exhalation contains at a concentration of only 1 ppm to 1 ppt.

Accordingly, a prior analyzing device comprises a mechanism to condense the chemical substance contained in the sample collected noninvasively.

For example, the exhalation analyzing device disclosed in the patent document 2 analyzes the resulted condensate liquid after the exhalation is cooled and condensed in the analyzing device. FIG. 25 shows the exhalation analyzing device disclosed in the patent document 1.

The exhalation blown by a patient is cooled and the resulted condensate liquid is collected with the exhalation analyzing device 901 shown in FIG. 25. The exhalation analyzing device 901 comprises a condensate part 902, a recover well 903, an inlet, an outlet, a curvature 904, and a flow path structure 905. The exhalation is injected from the inlet into the exhalation analyzing device 901, and discharged from the outlet. The condensate liquid of the exhalation is generated at the outer peripheral surface of the condensate part 902, which has the curvature 904. Since almost all the surface of the condensate part 902 is hydrophobic, the droplets of the resulted condensate liquid moves to the lower end of the condensate part 902. The droplets accumulated at the lower end drops into the recover well 903.

The period to obtain the condensate liquid at an amount necessary for analysis is required according to the exhalation analyzing device shown in FIG. 25. However, it is relatively simple to handle the device. Accordingly, the analysis of the exhalation component with the exhalation analyzing device shown in FIG. 25 is one of generally used procedures.

Patent Document 3 discloses an example of a condensing method using electrostatic atomization. According to this procedure, by atomizing electro-statically tenuous nonvolatile biomolecule, the solvent in a mist is evaporated to condense the biomolecule contained in the dilution. The procedure can be used for condensing and analyzing nonvolatile component contained in urine. FIG. 26 shows a condensation means of the biomolecule disclosed in the patent document 3.

A deposition of nonvolatile substances containing huge biomolecule is formed with the electrostatic atomizing device 906 shown in FIG. 26. The deposition is used to measure the interaction between the deposition of nonvolatile substances and other substances. Patent Document 3 discloses that the deposition according to electrostatic atomizing method of a living molecule can be used as a means for micro-condensing a biomolecule dilution.

Patent document 4 discloses a device for analyzing volatile component in exhalation or urine more easily with electrostatic atomization. In the analyzing device, after vapor and chemical substances are condensed into an atomizing electrode part, they are configured to be electric-charged fine particles. The chemical substance is condensed while electric-charged fine particles move from the atomizing electrode part to a detector of the chemical substance.

Citation List

[Patent Document]
  [Patent Document 1]
  Japanese Laid-open patent publication No. 2000-504114 (pages 11-12)
  [Patent Document 2]
  US 2007/173731 (Page 13, FIG. 20)
  [Patent Document 3]
  Japanese Laid-open patent publication No. 2002-511792 (page 78, FIG. 9)
  [Patent Document 4]
  WO 2009/057256 (Page 1/12, FIG. 1)
  [Patent Document 5]
  Japanese Laid-open patent publication No. 2008-128955 (Particularly, front page, FIG. 6(*d*), and paragraph 0055)
[Non-Patent Document]
  [Non-Patent Document 1]
  THE LANCET, 353, pp. 1930-1933(1999)

[Non-Patent Document 2]
ANALYTICAL BIOCHEMISTRY 247, pp. 272-278 (1997)

[Non-Patent Document 3]
The American Journal of Cardiology pp. 1593-1594 (2004)

[Non-Patent Document 4]
Respiratory Physiology & Neurobiology 145, pp. 295-300 (2005)

SUMMARY OF INVENTION

Technical Problem

The electric-charged fine particles are collected into the detector of the chemical substance with electrostatic force in the prior analyzing device using the electrostatic atomizing method. In order to prevent the detector of the chemical substance from (1) being damaged due to collision with the electric-charged fine particles and (2) being damaged electrically due to application of high voltage, the analyzing device using the electrostatic atomizing method has a structure in which the recovery equipment and the detector of the chemical substance are divided. Accordingly, the condensate liquid composed of the collected electric-charged fine particles is carried by a carrying means such as a syringe or a capillary (Paragraph (0130)-(0134) of the Patent Document 4).

However, a portion of the condensate liquid is remained inside the syringe, when the condensate liquid is carried from the recoverer of the chemical substance to the detector of the chemical substance using the carrying means such as a syringe or a capillary. Accordingly, there is a problem that an ultralow amount of the chemical substance contained in the condensate liquid at an amount of only approximately 1 micrometer is drained during the carrying.

The present invention solves the above-mentioned problems. The present invention is directed to a method for detecting efficiently and easily the ultralow amount of the chemical substance contained in a gas sample. The purpose of the present invention is to decline the damage to the electrode for detecting the chemical substance when the electric-charged fine particles are collected. Another purpose of the present invention is to suppress loss of the chemical substance on the measuring.

Solution to Problem

The present invention solving the prior problem(s) relates to a method for detecting a chemical substance contained in a gas sample using an analyzing device, comprising the following steps (a) to (h):

a step (a) of preparing the analyzing device, wherein,
the analyzing device (101) comprises:
a vessel (100),
an inlet (102) for injecting the gas sample, and provided with the vessel (100),
an atomizing electrode (105) inside the vessel (101),
a cooling part (104) cooling the atomizing electrode (105),
a counter electrode (107) provided in the vessel (101),
an intermediate electrode (106) disposed between the atomizing electrode (105) and the counter electrode (107), and
a liquid detector (111), a step (b) of injecting the gas sample from the inlet (102) to the vessel (100), wherein
the gas sample contains vapor,
a step (c) of cooling the atomizing electrode (105) with the cooling part (104) to condense the gas sample into a first condensate liquid (204) on the surface of the atomizing electrode (105),
a step (d) of applying a potential difference between the atomizing electrode (105) and the intermediate electrode (106) to cause the first condensate liquid to be electric-charged fine particles (205),
a step (e) of recovering the electric-charged fine particles (205) on the surface of the counter electrode (107) by applying a potential difference between the intermediate electrode (106) and the counter electrode (107) to obtain a second condensate liquid (206),
a step (f) of detecting with the liquid detector (111) that the second condensate liquid (206) has not less than predetermined amount.
a step (g) of inserting a support (100) comprising a detecting electrode (109) into the vessel (101) to bring the detecting electrode (109) into contact with the second condensate liquid (206), and
a step (h) of applying current voltage between the counter electrode (107) and the detecting electrode (109) to detect the chemical substance on the basis of the value of the generated current.

It is preferred that the analyzing device comprises a second cooling part cooling the counter electrode, wherein the counter electrode is cooled by the second cooling part to no higher than the dew-point temperature of water vapor in the step (e).

It is preferred that the step (e) is stopped when it is detected that the second condensate liquid has not less than the predetermined amount in the step (f).

It is preferred that the step (g) and the step (h) are preferred after the step (e) is stopped.

It is preferred that the potential of the counter electrode is equal to the potential of the detecting electrode in the step (h).

The objects described in the foregoing, other objects, features and advantages of the present invention will be apparent from the following detailed description of preferred embodiments with reference to attached drawings.

ADVANTAGEOUS EFFECTS OF INVENTION

According to the chemical substance analyzing method of the present invention, necessary and sufficient condensate liquid is obtained efficiently since the amount of the condensate liquid is detected by the liquid detecting part. In addition, since the detecting electrode moves to the position of the condensate liquid at a necessary amount after it is detected that the condensate liquid has been obtained, the damage to the detecting electrode due to the collision of the electric-charged fine particles is lowered. Furthermore, the loss of the condensate liquid on the carrying can be suppressed.

DESCRIPTION OF EMBODIMENTS

Hereinafter, Embodiments of the present invention will be explained with appropriate reference to the drawings.

Embodiment 1

Figure 1:
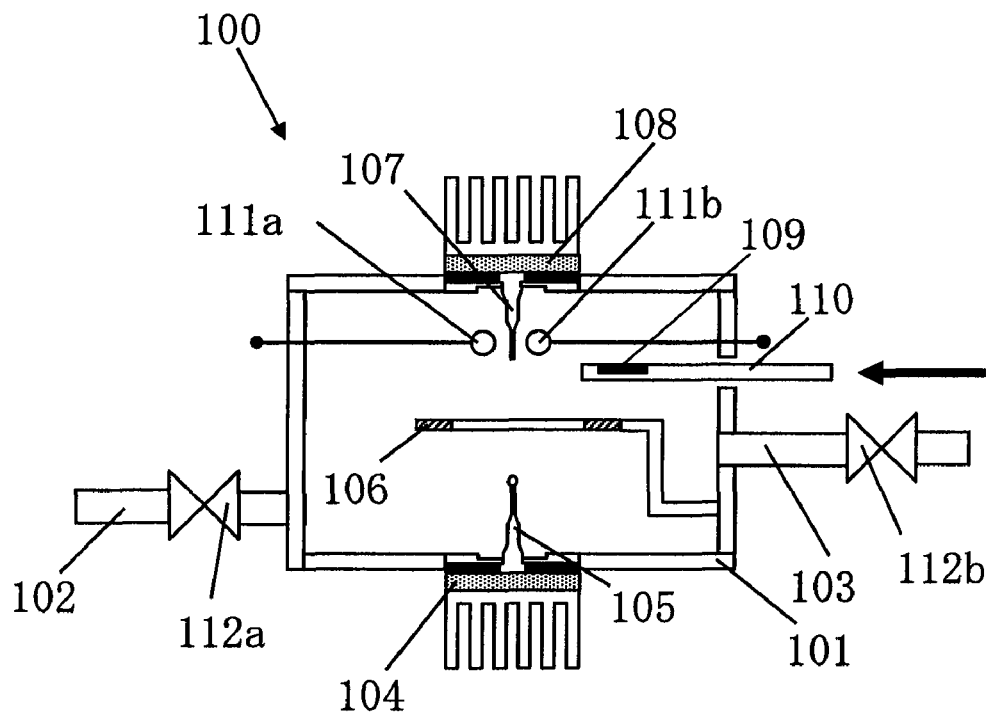
FIG. 1 shows a structural drawing of the analyzing device according to the embodiment 1.
Figure 2:
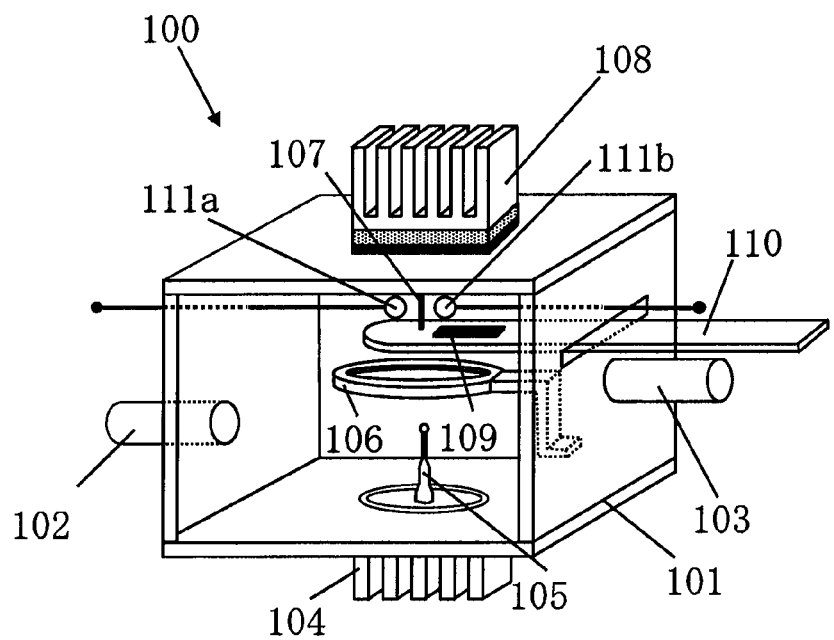
FIG. 2 shows a perspective view of the analyzing device shown in FIG. 1.

FIG. 1 shows a structural view illustrating an analyzing device according to Embodiment 1 of the present invention. FIG. 2 shows a perspective view of the analyzing device 100 shown in FIG. 1.

In the present Embodiment, a method for electrostatic spray of gas sample may be carried out in a substantially similar manner to the method disclosed in Japanese Patent Application No. 2008-556597, No. 2008-225521, and No. 2009-036137, which are filed in the name of the same inventor(s) as that(those) of the present application.

The largest difference between a method for analyzing a chemical substance of the present invention and the analyzing method disclosed in Japanese Patent Application No. 2008-556597, No. 2008-225521, and No. 2009-036137 is to detect amount of a condensed liquid by providing a liquid detecting part. Furthermore, another difference between the method for analyzing the chemical substance of the present invention and the analyzing method disclosed in Japanese Patent Application No. 2008-556597, No. 2008-225521, and No. 2009-036137 is to detect a chemical substance contained in the condensed liquid by moving a detecting electrode to the position of the condensed liquid and applying direct current in the condition where the condensed liquid is in contact with a counter electrode and a detecting electrode.

<Step (a)>

The analyzing device 100 is described below.

A container 101 serves as a partition wall. Any substance fails to run from/to the outside through the partition wall. The vessel 101 may have a shape of either a rectangular solid, or may be anyone of polyhedra, spindles, spheres, and flow paths. It is preferred that retention of the gas sample in a part of the vessel 101 can be prevented. The volume of the vessel 101 is preferably no less than 10 pL and no greater than 100 mL. The volume of the vessel 101 is more preferably no less than 1 mL and no greater than 30 mL.

The material of the vessel 101 is desirably accompanied by less adsorption gas or included gas. The material of the vessel 101 is most preferably a metal. The metal is preferably stainless; however, aluminum or brass is also acceptable. The material of the vessel 101 may also be an inorganic material other than metal. The material of the vessel 101 may also be glass, silicon, alumina, sapphire, quartz glass, borosilicic acid glass, silicon nitride, alumina, or silicon carbide. The material of the vessel 101 may be one produced by covering a silicon substrate with silicon dioxide or silicon nitride, or tantalum oxide.

The material of the vessel 101 may also be an organic material. Preferably, the material of the vessel 101 may be acryl, polyethylene terephthalate, polypropylene, polyester, polycarbonate, fluorine resin, polydimethyl siloxane, PEEK (registered trademark), or Teflon (registered trademark). When an organic material is used as the material of the vessel 101, the outer peripheral surface of the vessel 101 is more preferably coated with a metal thin film. As the metal thin film, a material having superior gas barrier properties is preferred. The material of the vessel 101 may be one of the materials described in the foregoing, or any combination of multiple materials of those.

The vessel 101 is preferably hard. It may be soft as in the case of an air bag, balloon, flexible tube, or syringe.

An inlet 102 is provided so as to be in communication with the vessel 101. The inlet 102 is used for injecting the gas sample into the vessel 101. It is preferred that the inlet 102 be provided at a position enabling the gas sample to be rapidly injected into the vessel 101. It is preferred that the inlet 102 be provided at a position enabling the gas sample to be injected uniformly into the vessel 101. Namely, it is preferred that the inlet 102 is provided at the side wall of the vessel 101.

The inlet 102 preferably has a shape that enables the gas sample to be uniformly injected into the vessel 101. The inlet 102 may also have a large number of through-holes like an air shower device. In the present invention, the size and the material of the inlet 102 are not limited. The shape of the inlet 102 may be of a straight tube as shown in FIG. 1, or may be provided with a branched portion along the path. The inlet 102 maybe provided either at one site, or at multiple sites.

An outlet 103 is provided at the other end of the vessel 101. The outlet 103 is used for discharging the excess gas sample from the gas sample filled in the vessel 101. The outlet 103 is preferably provided at a position enabling the gas sample filled in the vessel 101 to be rapidly discharged. The outlet 103 is preferably disposed at the position opposite to the inlet 102. In the present invention, the shape, the size and the material of the outlet 103 are not limited. The shape of the outlet 103 may be of a straight tube as shown in FIG. 1, or may be provided with a branched portion along the path. The outlet 103 may be provided either at one site, or at multiple sites.

A cooling part 104 has a function of cooling an atomizing electrode 105, which is described later. In FIG. 1, the cooling part 104 is adjacent to the atomizing electrode 105, and provided at a portion of the outer surface of the vessel 101. The cooling part 104 enables the gas sample to be cooled to a temperature no higher than the dew-point of water vapor. The cooling part 104 is most preferably a thermoelectric element. The cooling part 104 may be a heat pipe in which a refrigerant is used, a heat air transfer element, or a cooling fan. The area of the cooling part 104 is preferably small since it is enough as long as the electrode can be cooled. In light of reduction of the electric power consumption, the area of the cooling part 104 is preferably as small as possible. For the purpose of efficiently cooling the electrode 105, a relief structure is preferably provided on the surface of the cooling part 104. A porous material may be also provided on the surface of the cooling part 104. The position of the cooling part 104 is most preferably the bottom part of the vessel 101, but may be the lateral part or top part. Alternatively, a plurality of the cooling parts 104 may be also provided at the positions including these in combination.

In order to suppress thermal conduction, the contact area of the cooling part 104 with the vessel 101 is preferably small, and specifically, the contact area is preferably no less than 100 $\mu m^2$ and no greater than 5 $mm^2$.

In FIG. 1, the atomizing electrode 105 is provided at a position where it comes in contact with the cooling part 104; however, it may be provided apart from the cooling part 104. The atomizing electrode 105 is cooled by the cooling part 104 to no higher than the dew-point temperature of water vapor. It is preferred that the atomizing electrode 105 be in direct contact with the cooling part 104. It may be in contact via a material having a great thermal conductivity. The material having a great thermal conductivity is preferably a thermal conductive sheet, thermal conductive resin, metal plate, grease, or metal paste.

The atomizing electrode 105 is preferably positioned on the bottom surface of the vessel 101, most preferably positioned at the center of the bottom surface. The atomizing electrode 105 maybe also positioned on the lateral face or the above face of the vessel 101. When the atomizing electrode 105 is provided at the bottom surface, it may be positioned no less than 10 mm away from the lateral face of the vessel 101. The atomizing electrode 105 is provided at the bottom surface, the tip of the atomizing electrode 105 is preferably directed upward.

The shape of the atomizing electrode 105 is preferably needle-like. The length of the needle is preferably no less than 3 mm and no greater than 10 mm. The atomizing electrode 105 may be solid, hollow, or porous. A relief structure or a groove structure may be also provided on the surface of the atomizing electrode 105. The tip of the atomizing electrode 105 may be provided with a spherical protrusion. The whole of the atomizing electrode 105 is preferably cooled to no higher than the dew-point temperature of water vapor.

The material of the atomizing electrode 105 is preferably a good thermal conductive material, and most preferably a metal. The metal may be an element metal such as copper, aluminum, nickel, tungsten, molybdenum, titanium, or tantalum, and an alloy or an intermetallic compound including two or more element metals in combination such as, for example, stainless, copper tungsten, copper-zinc alloys, brass, high-speed steel, or carbide may be also acceptable.

The material of the atomizing electrode 105 may be an inorganic material. The material of the atomizing electrode 105 is preferably a semiconductor or a carbon material. The material of the atomizing electrode 105 may be $LaB_6$, SiC, WC, silicon, gallium arsenide, gallium nitride, SiC, a carbon nanotube, graphene, or graphite. The material of the atomizing electrode 105 may be one of the aforementioned materials, or two or more of them may be used in combination.

In order to suppress abrasion of the atomizing electrode 105 and facilitate transfer of electrons between the surface of the atomizing electrode 105 and the condensed liquid, the surface of the atomizing electrode 105 is preferably covered. The material for covering the atomizing electrode 105 is preferably a metal, a semiconductor, an inorganic material such as carbon material. As the metal, gold, platinum, aluminum, nickel, or chromium is preferred. As the inorganic material other than the metal, $LaB_6$, SiC, WC, silicon, gallium arsenide, gallium nitride, SiC, a carbon nanotube, graphene, or graphite is preferred. The atomizing electrode 105 may be covered by a single layer of the aforementioned inorganic material, or a laminate of two or more of them.

The number of the atomizing electrode 105 maybe one, or two or more. When the atomizing electrode 105 is provided in the number of two or more, they may be arranged one-dimensionally like linear, two-dimensionally like circular, parabolic, elliptic, square lattice-like, orthorhombic lattice-like, closest packed lattice-like, radial, random or the like, or may be arranged three-dimensionally like spherical, parabolic, oblate or sphere.

The surface of the atomizing electrode 105 is preferably hydrophilic, but may be water-repellent.

An intermediate electrode 106 is provided inside the vessel 101. A high voltage is applied between the intermediate electrode 106 and the atomizing electrode 105 to generate potential difference between the intermediate electrode 106 and the atomizing electrode 105. As a result, the condensed liquid becomes electric-charged fine particles. The shape of the intermediate electrode 106 is most preferably toric; however, it may be polygonal such as rectangular or trapezoidal. The shape of the intermediate electrode 106 is preferably flat; however, it maybe hemisphere or domal. When the intermediate electrode 106 is toric, the external diameter of the intermediate electrode 106 is preferably no less than 10 mm and no greater than 30 mm, while the internal diameter of the intermediate electrode 106 is preferably no less than 1 mm and no greater than 9.8 mm.

The thickness of the intermediate electrode 106 is preferably no less than 0.1 mm and no greater than 5 mm. At the intermediate electrode 106, a slit and a through-hole through which the chemical substance pass preferably formed. In the present invention, the shape of the intermediate electrode 106 is not limited; however, it is preferred the intermediate electrode 106 is electrically isolated from the vessel 101.

The distance between the intermediate electrode 106 and the atomizing electrode 105 is preferably no less than 3 mm and no greater than 10 mm. The intermediate electrode 106 may be movable with respect to the vessel 101. When the intermediate electrode 106 is toric, the atomizing electrode 105 is preferably provided on a straight line that passes the center of the intermediate electrode 106 and crosses vertically with the plane of the intermediate electrode 106.

The intermediate electrode 106 is preferably insulated electrically from the vessel 101.

The material of the intermediate electrode 106 is preferably a conductor. The material of the intermediate electrode 106 is most preferably a metal. The metal is preferably an element metal such as copper, aluminum, nickel, tungsten, molybdenum, titanium or tantalum. The material of the intermediate electrode 106 may be an alloy or an intermetallic compound including two or more element metals. The intermediate electrode 106 may be formed of stainless, copper tungsten, brass, high-speed steel, carbide alloy.

The material of the intermediate electrode 106 may be an inorganic material other than a metal. The material of the intermediate electrode 106 is preferably a semiconductor, a carbon material, or an insulator. The material of the intermediate electrode 106 may be $LaB_6$, SiC, WC, silicon, gallium arsenide, gallium nitride, SiC, a carbon nanotube, graphene, graphite, alumina, sapphire, silicon oxide, ceramics, glass, or a polymer. The material of the intermediate electrode 106 may be one of the aforementioned materials, or two or more of them maybe used in combination.

The material of the intermediate electrode 106 is preferably a good thermal conductor. It is preferred that the intermediate electrode 106 be heated to no less than the dew-point temperature of water vapor such that an unwanted condensate liquid does not adhere on the surface of the intermediate electrode 106.

In order to suppress abrasion of the intermediate electrode 106, the surface of the intermediate electrode 106 is preferably covered. The material for covering the intermediate electrode 106 may be a similar inorganic material to that of the atomizing electrode 105. The intermediate electrode 106 maybe covered with a single layer of the inorganic material, or a laminate of two or more of them.

The surface of the intermediate electrode 106 is preferably hydrophilic, but may be water-repellent.

The number of the intermediate electrode 106 maybe one, or two or more. When the intermediate electrode 106 is provided in the number of two or more, they may be arranged one-dimensionally like linear, two-dimensionally like circular, parabolic, elliptic, square lattice-like, orthorhombic lattice-like, closest packed lattice-like, radial, or random, or may be arranged three-dimensionally like spherical, parabolic, or oblate sphere.

A counter electrode 107 is provided in the vessel 101 and at the opposite side of the atomizing electrode 105. The intermediate electrode 106 is interposed between the counter electrode 107 and the atomizing electrode 105. The counter electrode 107 is used for recovering the electric-charged fine particles. The material of the counter electrode 107 may be similar material to that of the intermediate electrode 106. The material of the counter electrode 107 may be one of the aforementioned materials, or two or more of them may be used in combination.

It is preferred that the counter electrode 107 reflects light. It is preferred that the counter electrode 107 reflects visible light. It is more preferred that the surface of the counter electrode 107 is mirror plane. The counter electrode 107 is preferably cooled by a second cooling part 108 to no higher than the dew-point temperature of water vapor.

In FIG. 1, the counter electrode 107 is provided at the position where it is in contact with the second cooling part 108; however, it may be provided apart from the second cooling part 108. Preferably, the counter electrode 107 is in directly contact with the second cooling part 108. The counter electrode 107 may be in contact with the second cooling part 108 via a material having a good thermal conductivity. The material having a good thermal conductivity is preferably a thermal conductive sheet, thermal conductive resin, metal plate, grease, or metal paste.

The counter electrode 107 is preferably an electrochemical electrode. The counter electrode 107 is preferably platinum, gold, glassy carbon, carbon paste, palladium paste, Ag.AgCl paste, nickel, titanium, chromium, silver, silver chloride, Ag/AgCl, saturated calomel electrode or gel electrode.

The counter electrode 107 is preferably provided at the above face of the vessel 101. The counter electrode 107 is most preferably provided at the center of the above face of the vessel 101. The tip of the counter electrode 107 is preferably directed downwardly. The counter electrode 107 is preferably provided apart not less than 10 mm apart from the lateral of the vessel 101. The counter electrode 107 may be provided at the lateral or bottom of the vessel 101.

The shape of the counter electrode 107 is preferably needle-like. The length of the needle is preferably no less than 3 mm and no greater than 10 mm. The shape of the counter electrode 107 may be solid, hollow, or porous. A relief structure or a groove structure may be also provided on the surface of the counter electrode 107. The tip of the counter electrode 107 may be provided with a spherical protrusion. The whole of the counter electrode 107 is preferably cooled to no higher than the dew-point temperature of water vapor.

The second cooling part 108 has a function to cool the counter electrode 107. In FIG. 1, the second cooling part 108 is provided adjacently to the counter electrode 107 and provided at one end of the vessel 101. The second cooling part 108 allows the counter electrode to be cooled to no higher than the dew-point temperature of water vapor. The second cooling part 108 is most preferably a thermoelectric device. The second cooling part 108 may be a heat pipe in which a refrigerant is used, a heat air transfer element, or a cooling fan. The area of the second cooling part 108 is preferably small since it is enough as long as the electrode can be cooled. In light of reduction of the electric power consumption, the area of the second cooling part 108 is preferably as small as possible. For the purpose of efficiently cooling the counter electrode 107, a relief structure is preferably provided on the surface of the second cooling part 108. A porous material may be also provided on the surface of the second cooling part 108. The position of the second cooling part 108 is most preferably the above part of the vessel 101, but may be at the lateral or bottom part. Alternatively, a plurality of the second cooling parts 108 maybe also provided at the positions including these in combination.

To suppress heat conduction, it is preferred that the second cooling part 108 has small contact area with the vessel 101. The area is preferably not less than 100 $\mu m^2$ and not more than 5 $mm^2$.

The counter electrode 109 is composed of metal such as stainless, alminium, or brass.

The detecting electrode 109 is provided on the support 110. The support is movable. It is preferred that the support 101 moves automatically; however, it may move manually or semi-automatically. The detecting electrode 109 is detachable from the vessel 101. It is preferred that the detecting electrode 109 is detached manually; however, it may be detached automatically or semi-automatically.

The shape of the support 110 is most preferably a board. The shape of the support 110 may be a rod, a disk, a rectangular parallelepiped, a square, a circle, or a trapezoid. In light of handling the support 110, it is preferred that the support 110 has a longitudinal length of not less than 5 mm and not more than 100 mm. It is preferred that the support 110 has a width of not less than 5 mm and not more than 100 mm.

The vessel 101 preferably has a mounting mechanism of the support 110. The mounting mechanism of the support 110 is preferably a slit provided in the vessel 101. The mounting mechanism of the support 110 may be a stage, a tube, or other mounting mechanism provided in the vessel 101. The mounting mechanism of the support 110 is preferably provided in the neighborhood of the counter electrode 107. The mounting mechanism of the support 110 is preferably provided on the imaginary line extended along the moving direction of the support 110. A valve is preferably provided to the mounting mechanism of the support 110 not to leak the chemical substance in the vessel 101. In order to leak the chemical substance in the vessel 101, the mounting mechanism of the support 110 has an opening with an area of not less than 10 $\mu m^2$ and not more than 10 $mm^2$.

The number of the detecting electrode 109 provided at the support 110 may be one or more. When a plurality of the detecting electrodes are provided at the support 110, identical kinds of a plurality of the electrodes may be provided, or a plurality kind of the electrodes may be provided. It is preferable that the detecting electrode 109 has a longitudinal length of not less than 10 nm and not more than 100 mm.

Figure 3:
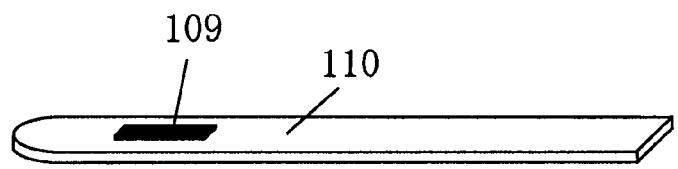
FIG. 3 shows a perspective view of the detecting electrode according to the embodiment 1.

As shown in FIG. 3, the tip of the support 110 has a curvature. Since the tip of the support 110 has a curvature, the support 110 can be mounted easily to the vessel 101. As shown in FIG. 3, the tip of the support 110 is preferably semicircle; however, it may be polygonal, trapezoidal, or triangular. It is preferred that the support 110 has a thickness of not less than 50 $\mu m$ and not more than 2 mm. The material of the support 110 may be inorganic or organic.

As shown in FIG. 3, the detecting electrode 109 is most preferably provided at the top surface of the support 110. The detecting electrode 109 is preferably provided at the neighborhood of the tip of the support 110. The detecting electrode 109 may be provided at the lateral or bottom of the support 110. The direction of the detecting electrode 109 can be varied by rotating the support 110. The support 110 with a longitudinal axis shown in FIG. 3 is preferably spun about the longitudinal axis.

The material of the support 110 may be an inorganic material or an organic material. The material of the support 110 preferably has insulation. Preferably, the inorganic material includes glass, silicon, alumina, sapphire, quartz glass, borosilicate glass, silicon nitride, and silicon carbide. The material of the support 110 may be an inorganic material coated by silicon dioxide, silicon nitride, or tantalum oxide on a silicon substrate. The organic material includes acryl, polyethylene terephthalate, polypropylene, polyester, polycarbonate, fluorine resin, polydimethyl siloxane, PEEK (registered trademark), or Teflon (registered trademark). The material of the support 110 may be one of the materials described in the foregoing, or any combination of multiple materials of those.

The surface of the support 110 is preferably water-repellent; however, it may be hydrophilic.

A liquid detecting part 111 is preferably provided around the counter electrode 107. It is more preferable that the liquid detecting part 111 is provided at the neighborhood of the tip of the counter electrode 107. It preferable that the distance between the liquid detecting part 111 and the counter electrode 107 is not less than 1 mm and the not more than 50 mm. It preferable that the distance between the liquid detecting part 111 and the counter electrode 107 is not less than 1 mm and the not more than 2 mm.

It is most preferable that the liquid detecting part 111 is an optical detector, since it can detect the existence of the condensed liquid noncontactly. The liquid detecting part 111 comprises a light-emitting part 111a and a light-receiving part 111b. The liquid detecting part 111 may comprise an optical component such as a lens, an optical filter, or a mirror. The liquid detecting part 111 may detect light which has penetrated the condensed liquid. The liquid detecting part 111 may detect light which has been reflected or scattered by the condensed liquid. The liquid detecting part 111 may detect light which has been reflected by the outer peripheral surface of the counter electrode 107.

It is most preferable that the light-emitting part 111a is a light-emitting diode. The light-emitting part 111a may be a high-pressure mercury lamp, a halogen lamp, a tungsten lamp, a deuterium lamp, a metal halide lamp, a high-pressure sodium lamp, an HID lamp, or an electroluminescence lamp. In light of straight property and coherency, it is preferable that the light-emitting part 111a is a laser. A semiconductor laser, a solid laser, a liquid laser, a gas laser, or free-electron laser is preferred as the laser. It is preferred that the light emitted by the light-emitting part 111a is visible.

It is preferred that the light emitted by the light-emitting part 111a has a wavelength of not less than 360 nm and not more than 860 nm. It is preferred that the light emitted by the light-emitting part 111a is ultraviolet. It is preferred that the light emitted by the light-emitting part 111a has a wavelength of not less than 200 nm and not more than 380 nm. It is preferred that the light emitted by the light-emitting part 111a is infrared light. It is preferred that the light emitted by the light-emitting part 111a has a wavelength of not less than 700 nm and not more than 1 mm. In order to suppress the increase of the temperature of the inside of the device 100, the material of the vessel 101 is preferred to be a material which infrared light penetrates. The number of the light-emitting part 111a may be one,or may be two or more.

It is most preferable that light-receiving part 111b is a photodiode. It is preferable that photodiode includes a silicon photodiode, a silicon PIN photodiode, an avalanche photodiode, a CCD, or a CMOS image sensor. The light-receiving part 111b may be a photoresistor, a solar cell, a photomultiplier, a phototransistor, or pyroelectric detector. The number of the light-receiving part 111b may be one, or maybe two or more. The light-receiving parts 111b may be disposed like an array.

A light fiber may be connected to one end of the light-emitting part 111*a* and the other end of the light fiber may be positioned at the lateral of the counter electrode 107. A light fiber may be connected to one end of the light-receiving part 111*b* and the other end of the light fiber may be positioned at the lateral of the counter electrode 107.

The liquid detecting part 111 may be a light waveguide.

It is preferred that the inlet 102 and the outlet 103 are provided with the valve 112*a* and the valve 112*b*, respectively. It is preferable to render the vessel 101 closable by the valves 112*a* and 112*b*. The material, position and species of the valve 112*a* and the valve 112*b* are not limited. The valve 112*a* and the valve 112*b* may be valves for regulating the gas sample flow. The valve 112*a* and the valve 112*b* may be a non-return valve, or may be a stop valve.

FIG. 4 to FIG. 7 show an explanatory view illustrating the method for analyzing the chemical substance according to Embodiment 1. In FIG. 4 to FIG. 7, the same reference signs are used for the same constitution elements shown in FIG. 1 to FIG. 3, and their explanation is omitted.

Figure 4:
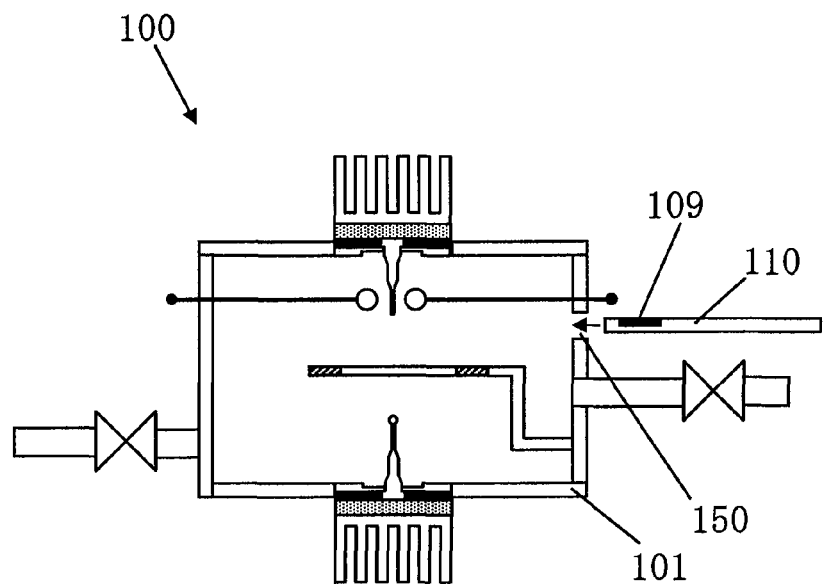
FIG. 4(A) shows how to mount the support 110 provided with the detective electrode 109 to the mounting mechanism 150 according to the embodiment 1.
FIG. 4(B) shows an explanatory drawing of step (b) in the embodiment 1.
Figure 4:
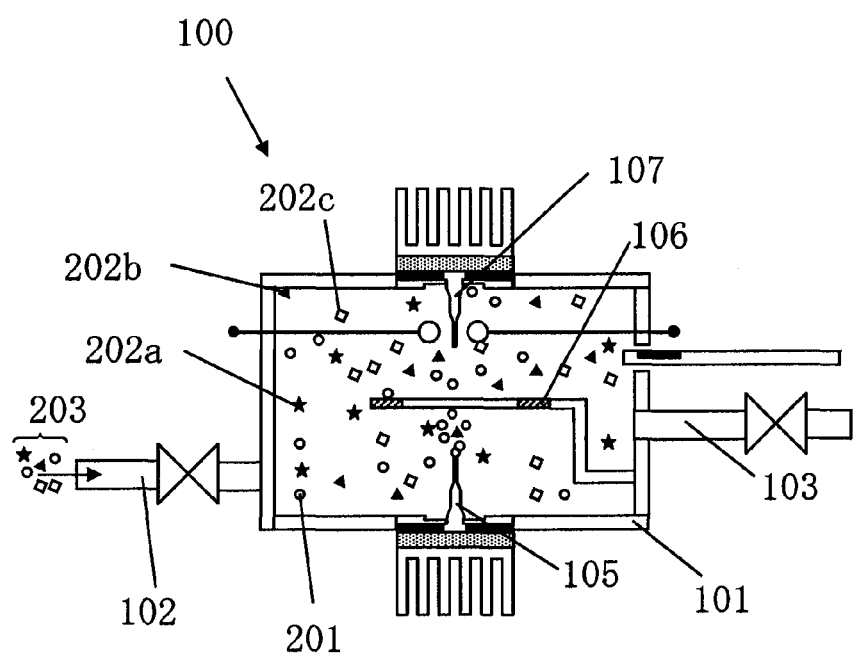
Figure 5:
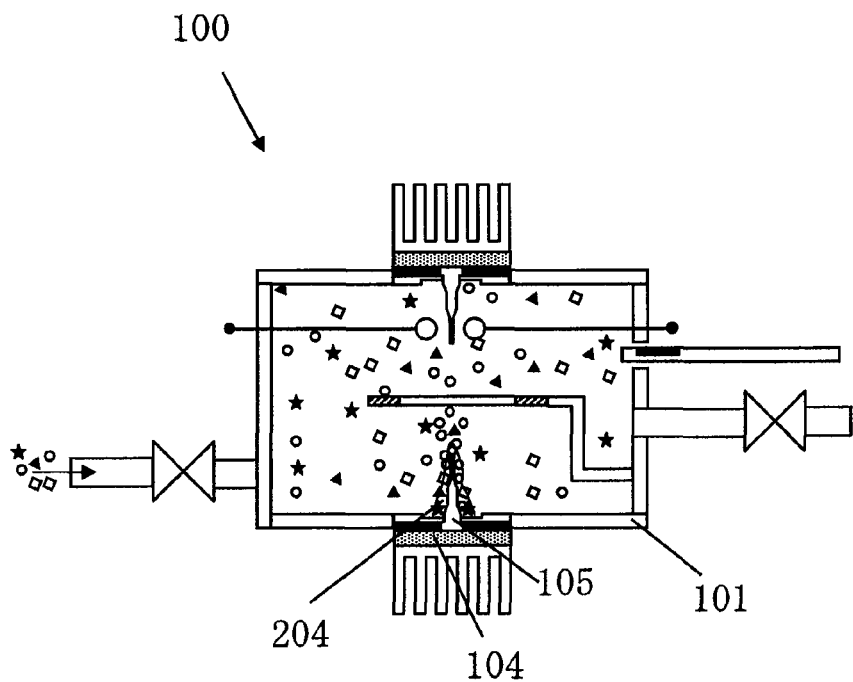
FIG. 5(A) shows an explanatory drawing of the step (c) in the embodiment 1.
FIG. 5(B) shows an explanatory drawing of the step (d) in the embodiment 1.
Figure 5:
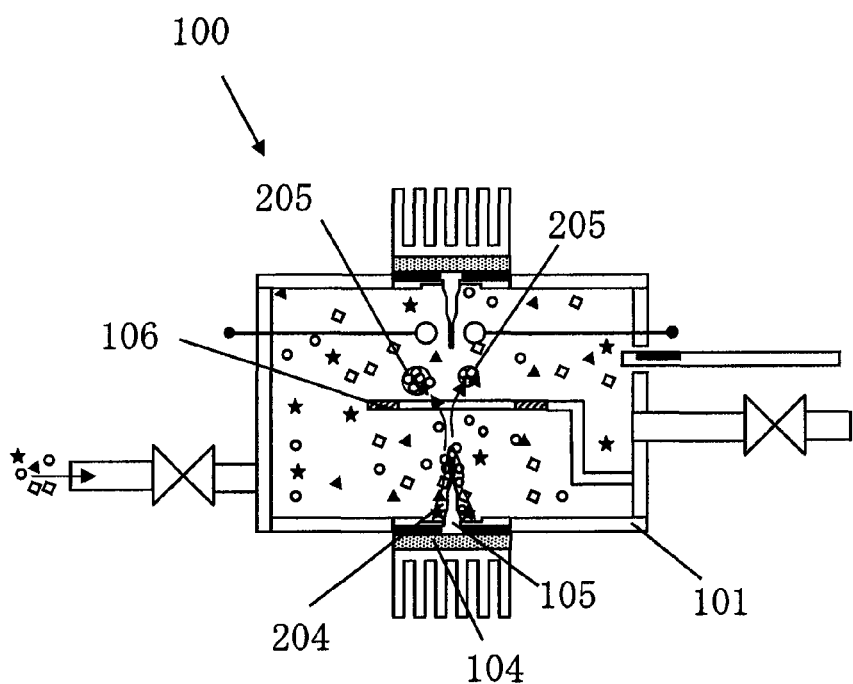
Figure 6:
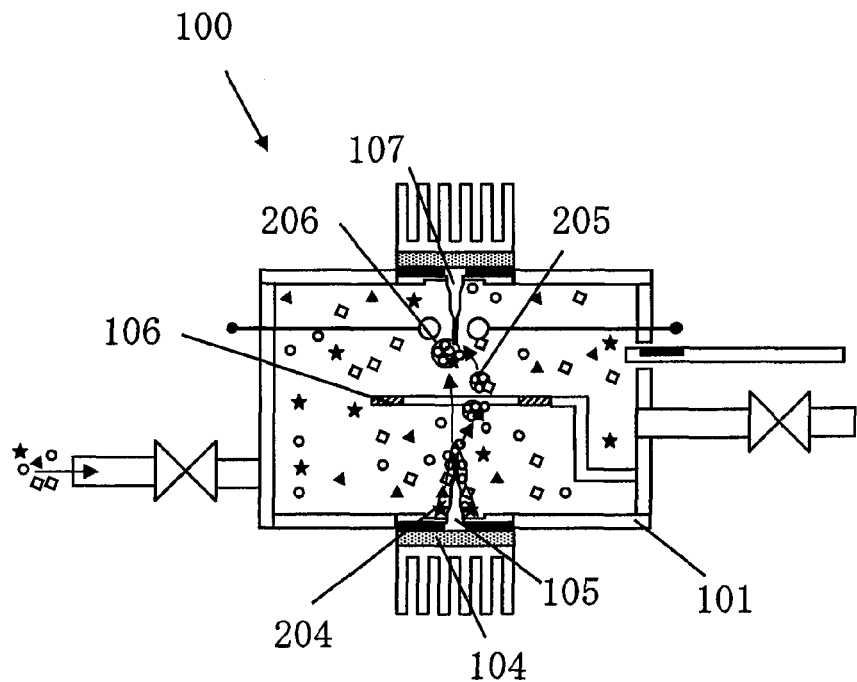
FIG. 6(A) shows an explanatory drawing of the step (e) in the embodiment 1.
FIG. 6(B) shows an explanatory drawing of the step (f) in the embodiment 1.
Figure 6:
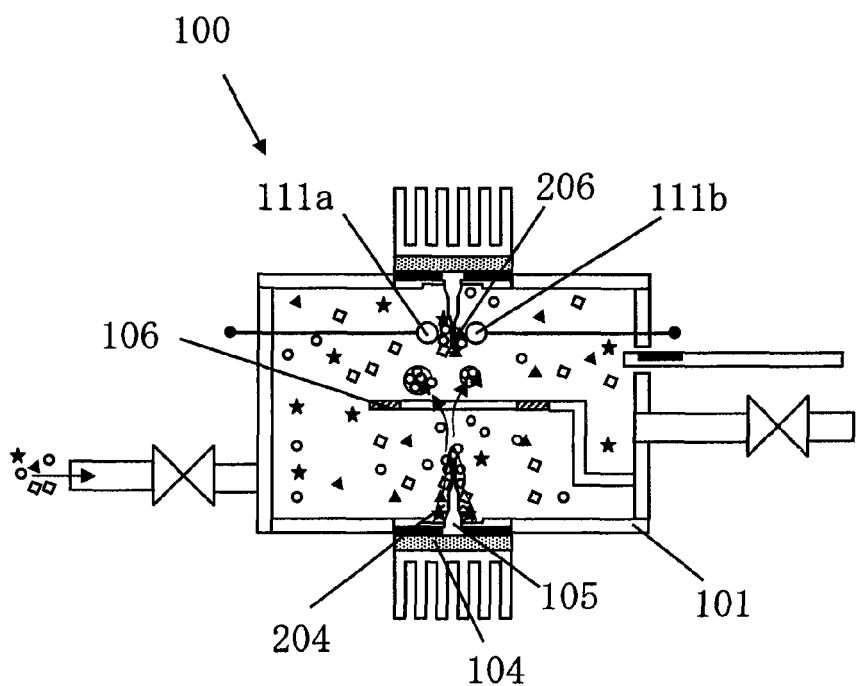
Figure 7:
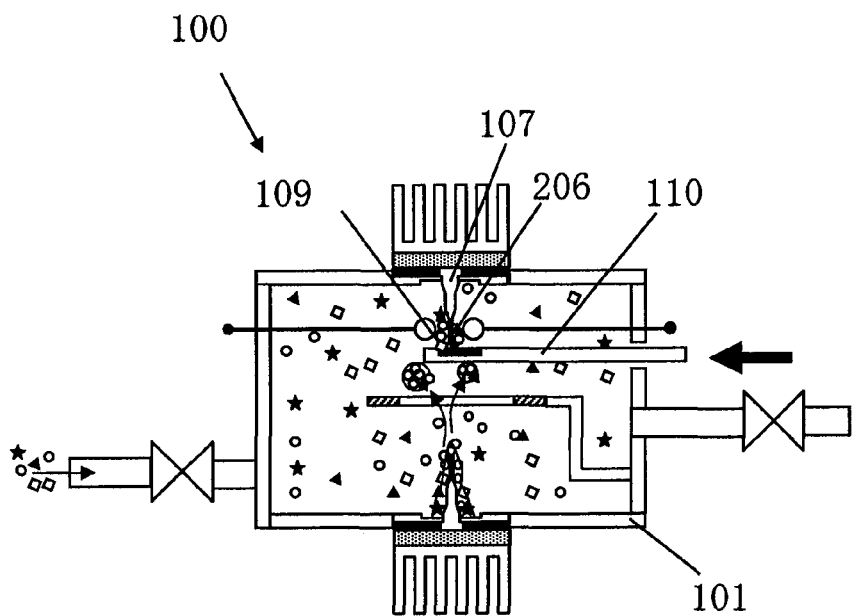
FIG. 7(A) shows an explanatory drawing of the step (g) in the embodiment 1.
FIG. 7(B) shows an explanatory drawing of the step (h) in the embodiment 1.
Figure 7:
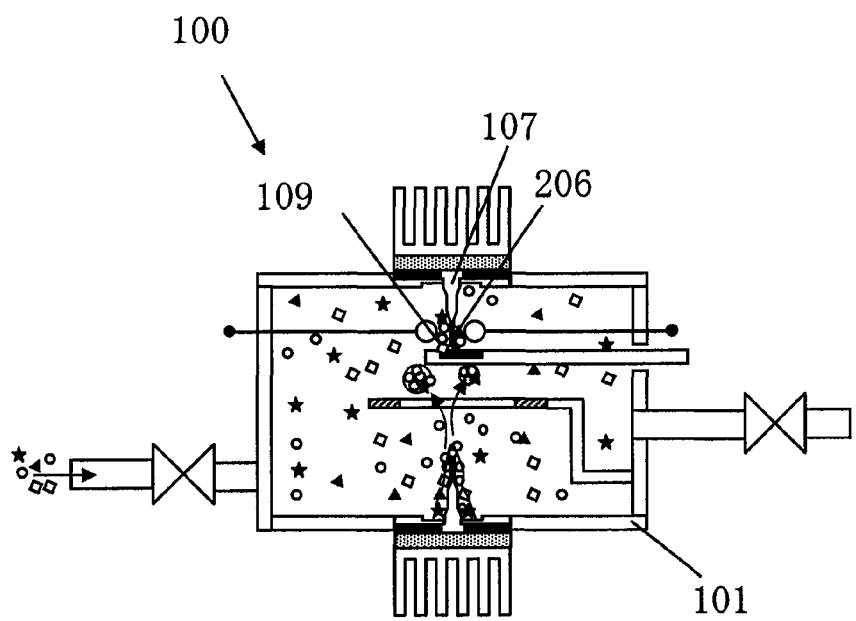

The support 110 provided with the detecting electrode 109 is mounted at one end of the vessel 101. The support 110 is preferably mounted to a mounting mechanism 150 of the vessel 101. The mounting mechanism 150 is preferably a slit. The mounting mechanism 150 has a guide to facilitate that the support 110 is mounted to the predetermined position. FIG. 4 shows how to mount the support provided with the detecting electrode 109 to the mounting mechanism 150. The detecting electrode 109 is preferably stood by the position not to be exposed by the electric-charged fine particle.

(Step (b))

In the step (b), a gas sample 203 containing water vapor 201 and a chemical substance 202 is injected into the vessel 101 through the inlet 102. FIG. 4(B) shows the step (b). In FIG. 4(B), three kinds of chemical substances 202*a*, 202*b*, and 202*c* represents as the chemical substance 202. One kind of the chemical 202*a* or two kinds of the chemical 202*a* may be used. In the present invention, the ratio of a plurality of the chemical substance 202 contained in the gas sample 203 is not limited.

It is preferred that the chemical substance 202 is an organic compound. It is preferred that the chemical substance 202 is a volatile organic compound. It is preferred that the chemical substance 202 is ketones, amines, alcohols, aromatic hydrocarbons, aldehydes, esters, organic acid, hydrogen sulfide, methylmercaptan, or disulfide. It is preferred that the chemical substance 202 is alkane, alkene, alkyne, diene, alicyclic hydrocarbon, allene, ether, carbonyl, carbanio, protein, polynuclear aromatic, heterocyclic, organic derivative, nucleic acid, ribonucleic acid, antibodies, biotic molecule, metabolites, isoprene, isoprenoid and their derivatives. The molecular weight of the chemical substance 202 is not less than 15 and not more than 500.

The gas sample 203 is gas sample preferably collected from a living body. The gas sample 203 is preferably generated from the liquid collected from the living body. It is most preferable that the liquid collected from the living body is urine. The liquid collected from the living body may be blood, perspiration, interstitial fluid, tear fluid, spit, or gastrointestinal tract fluid.

The gas sample 203 is preferably prepared by heating the liquid collected from the living body. The gas sample 203 is most preferably generated by heating urine. The gas sample 203 is preferably generated by heating blood, perspiration, interstitial fluid, tear fluid, spit, or gastrointestinal tract fluid. The gas sample 203 is preferably generated by heating the liquid collected from the living body at a temperature of not less than 30 degree Celsius and not more than 100 degree Celsius. By heating liquid collected from the living body at a temperature of not less than 30 degree Celsius, the chemical substance 202 contained in the liquid can be volatilized or evaporated. By heating liquid collected from the living body at a temperature of not more than 100 degree Celsius, the liquid is prevented from being boiled. It is more preferred that the liquid collected from the living body is heated at a temperature of 30 degree Celsius and not less than 60 degree Celsius to generate the gas sample 203, since deformation or decomposition of the protein, DNA, RNA or pepitide contained in the liquid is suppressed by heating the liquid collected from the living body at a temperature of not more than 60 degree Celsius.

The gas sample 203 may be generated by heading the liquid collected from the living body at a temperature of not less than 100 degree Celsius. By heating the liquid collected from the living body at a temperature of not less than 100 degree Celsius, the chemical substance 202 contained in the liquid can be volatilized or evaporated quickly.

It is preferred that the gas sample 203 is gas collected from the living body. The gas sample maybe exhalation, skin flesh gas, burp, colon gas, or fart.

It is preferred that the gas sample 203 is generated by heating a solid collected from the living body. It is preferred that the gas sample 203 is generated by heating a cell, a tissue, an internal organs, or hair. It is preferred that the gas sample 203 is generated by heating the solid collected from the living body at a temperature of not less than 30 degree Celsius and not more than 100 degree Celsius. By heating the solid collected from the living body at a temperature of not less than 30 degree Celsius, the chemical substance 202 contained in the solid can be volatilized or evaporated. By heating liquid collected from the living body at a temperature of not more than 100 degree Celsius, the solid is prevented from being boiled. It is more preferred that the solid collected from the living body is heated at a temperature of 30 degree Celsius and not less than 60 degree Celsius to generate the gas sample 203, since deformation or decomposition of the protein, DNA, RNA or peptide contained in the liquid can be suppressed by heating the liquid collected from the living body at a temperature of not more than 60 degree Celsius.

The gas sample 203 maybe generated by heading the solid collected from the living body at a temperature of not less than 100 degree Celsius. By heating the solid collected from the living body at a temperature of not less than 100 degree Celsius, the chemical substance 202 contained in the solid can be volatilized or evaporated quickly.

It is preferred that the gas sample 203 has relative humidity of not less than 50% and not more than 100%. It is more preferred that the gas sample 203 has relative humidity of not less than 80% and not more than 100%. In the step (b), vapor 201 may be added to the gas sample 203. The gas sample 203 preferably contains polar organic solvent. The preferred polar organic solvent is acetonitrile, isopropanol, formic acid, or acetic acid.

In the step (b), the gas sample 203 may be collided with the inner wall of the vessel 101. The gas sample 203 may be collided with the intermediate electrode 106. The gas sample 203 may be collided with the counter electrode 107.

It is preferred that the injection speed of the gas sample 203 is preferably no less than 10 sccm and no greater than 1000 sccm, and more preferably no less than 100 sccm and no greater than 500 sccm. The injection speed of the gas sample 203 is preferably constant, but the injection speed may vary.

The gas sample 203 in an amount of no less than 10 mL and no greater than 3000 mL is preferably injected into the vessel 101, and to inject the gas sample 203 in an amount of no less than 100 mL and no greater than 1000 mL is more preferred.

The gas sample 203 at a room temperature maybe injected into the vessel 101, or a warmed gas sample 203 maybe injected. The temperature of the gas sample 203 is preferably no less than 20° C. and no greater than 100° C., and more preferably no less than 25° C. and no greater than 40° C.

It is preferred that the gas sample 203 maybe injected by compressing the inlet 102 side, or by reducing the pressure of the outlet 103 side. In the step (b), the direction of the gas sample 203 flowing through the inlet 102 may be constant or may be varied. The direction of the gas sample 203 flow through the inlet 102 may be varied periodically.

In the step (b), it is preferred to open the valve 112a and the valve 112b. The flowing amount of the gas sample 203 may be regulated by opening or closing the valve 112a and the valve 112b appropriately.

Before the gas sample 203 is injected into the vessel 101, the interior of the vessel 101 is preferably filled with clean air, dry nitrogen, an inert gas, a standard gas having an approximately the same level of relative humidity to that of the gas sample 203, or a gas for calibration.

Excess of the gas sample 203 is preferably discharged from the outlet 103.

The pressure inside the vessel 101 is most preferably an ambient pressure, but the pressure of the vessel 101 may be reduced, or compression may be carried out. In the present invention, the pressure inside the vessel 101 is not limited.

In the following steps (c) to (h), the temperatures of the vessel 101, the inlet 102, the outlet 103, and the intermediate electrode 106 are preferably kept at no lower than the dew-point temperature of the water vapor so as to prevent the dew formation of the gas sample 203.

In the step (b), at least either of the atomizing electrode 105 or the counter electrode 107 may be cooled preliminarily. Before the step (b), at least either of the atomizing electrode 105 or the counter electrode 107 may be cooled preliminarily.

<Step (c)>

In the step (c), the atomizing electrode 105 is cooled by the cooling part 104 to no higher than the dew-point temperature of the water vapor 201. On the outer peripheral surface of the atomizing electrode 105, a first condensate liquid 204 containing the water vapor 201 and the chemical substance 202 is formed. In the initial stage of the step (c), the first condensate liquid 204 forms droplets on the outer peripheral surface of the atomizing electrode 105. In the stage of progress of the step (c), the outer peripheral surface of the atomizing electrode 105 is covered by the first condensate liquid 204. FIG. 5(A) shows the step(c).

In the step (c), it is preferred to regulate the temperature of the cooling part 104 so as not to increase the amount of the first condensate liquid 204 excessively. The temperature of the atomizing electrode 105 is preferably no lower than the solidifying point of the first condensate liquid 204.

The temperature of the atomizing electrode 105 is preferably no less than 0° C. and no greater than 20° C. By causing the temperature of the atomizing electrode 105 to be no less than 0° C., the first condensate liquid 204 is not frozen. By causing the temperature of the atomizing electrode 105 to be no greater than 20° C., the first condensate liquid 204 is formed quickly. It is more preferred that the temperature of the atomizing electrode 105 is not less than 0° C. and not more than 2° C. By causing the temperature of the atomizing electrode 105 to be not more than 2° C., the first condensate liquid 204 is formed quickly. If the first condensate liquid 204 is not frozen, the temperature of the atomizing electrode 105 may be not less than 0° C. to form the first condensate liquid 204 quickly.

In the step (c), it is preferred the injection of the gas sample is continued, the injection of the gas sample 203 may be stopped.

<Step (d)>

Next, in the step (d), a large number of electric-charged fine particles 205 are formed from the first condensate liquid 204. FIG. 5(B) shows the step (d).

The electric-charged fine particles 205 may be: a cluster including one to several ten molecules; fine particles including several ten to several hundred molecules; or may be a droplet including several hundred or more molecules. Alternatively, two or more types of these may be present admixed.

The electric-charged fine particles 205 may also include electrically neutral molecules, or ions or radicals derived from the gas sample 203. Alternatively, the electrically neutral molecules and the electrically neutral molecules may be present admixed in the electric-charged fine particles 205.

It is preferred that the electric-charged fine particles 205 are negatively charged. When the electric-charged fine particles 205 are negatively charged, the electronic affinity of the chemical substance 202 is preferably greater than the electronic affinity of water. The electric-charged fine particles 205 may be positively charged. When the electric-charged fine particles 205 are positively charged, the ionization energy of the chemical substance 202 is preferably smaller than the ionization energy of water.

The method for forming electric-charged fine particles from the first condensate liquid 204 is most preferably electrostatic spraying. The principle of the electrostatic spraying is as in the following. The first condensate liquid 204 is conveyed to the tip of the atomizing electrode 105 by the voltage applied between the atomizing electrode 105 and the intermediate electrode 106. The liquid level of the first condensate liquid 204 is elevated by the coulomb attractive force to form a conical shape toward the intermediate electrode 106 direction. When the condensation further proceeds on the outer peripheral surface of the atomizing electrode 105, the first condensate liquid 204 having a conical shape grows. Thereafter, the charge concentrates to the tip of the first condensate liquid 204, thereby leading to increase in the coulomb force. When this coulomb force exceeds the surface tension of water, the first condensate liquid 204 is disrupted and scatters to form the electric-charged fine particles 205.

In light of the stability of the electric-charged fine particle 205, the electric-charged fine particle 205 has a diameter of preferably no less than 1 nm and no greater than 30 nm.

The charge amount added to one of the electric-charged fine particles 205 is preferably no less than the same level and no greater than ten times of the elementary electric charge ($1.6 \times 10^{-19}$ C) per the fine particle.

The proportion of the chemical substance 202 with respect to the water vapor 201 in the electric-charged fine particle 205 is preferably higher than the proportion of the chemical substance 202 with respect to the water vapor 201 in the gas sample 203. The proportion of the chemical substance 202 with respect to the water vapor 201 in the electric-charged fine particles 205 may vary until reaching to the counter electrode 107, and preferably increases until reaching to the counter electrode 107.

In the step (d), a potential difference is generated between the atomizing electrode 105 and the intermediate electrode 106. It is most preferred that a direct current voltage is applied between the atomizing electrode 105 and the intermediate electrode 106. A voltage not causing corona discharge is preferably applied between the atomizing electrode 105 and the intermediate electrode 106, and specifically, a direct current voltage of no less than 4 kV and no greater than 6 kV is preferably applied. It is most preferred to apply a negative voltage to the atomizing electrode 105 with respect to the intermediate electrode 106, but a positive voltage may be applied. The intermediate electrode 106 is most preferably a GND electrode. In the step (d), an alternating current voltage may be applied between the atomizing electrode 105 and the intermediate electrode 106. A pulse voltage maybe applied between the atomizing electrode 105 and the intermediate electrode 106.

The value of the direct current voltage applied between the atomizing electrode 105 and the intermediate electrode 106 may be constant, or varying. The varying value is preferably regulated depending on the state of forming the electric-charged fine particles. With respect to the state of forming electric-charged fine particles, the electric current value running between the atomizing electrode 105 and the intermediate electrode 106 may be monitored, or the electric current value may be monitored with a dedicated electrode pair provided therefor. The current value flowing between the atomizing electrode 105 ant the intermediate electrode 106 is preferably regulated within not less than 1 pA and not less than 1 mA, more preferably, within not less than 1 µA and not less than 100 µA.

In the step (d), it is preferred that the step (b) and/or the step (c) are/is continued.

<Step (e)>

In the step (e), the potential difference is generated between the intermediate electrode 106 and the counter electrode 107. The electric-charged fine particles 205 are recovered into the counter electrode 107. FIG. 6(A) shows the step (e). In the step (e), the gas sample 203 may be recovered directly into the counter electrode 107. The amount of the gas sample 203 recovered into the counter electrode 107 is preferably smaller than the amount of the electric-charged fine particles 205 recovered into the counter electrode 107.

In the step (e), it is preferred that the step (b) is continued. In the step (e), it is preferred that the step (c) is continued. In the step (e), it is preferred that the step (d) is continued.

The electric-charged fine particles 205 are preferably recovered by an electromagnetic force or electrostatic force. A direct current voltage is preferably applied to the counter electrode 107 with respect to the intermediate electrode 106. The direct current voltage is preferably no less than 0.01 kV and no greater than 6 kV, and more preferably no less than 0.01 kV and no greater than 0.6 kV. When the electric-charged fine particles 205 are negatively charged, a positive voltage is preferably applied to the counter electrode 107. To the contrary, when the electric-charged fine particles 205 are positively charged, a negative voltage is preferably applied to the counter electrode 107. The voltage is preferably applied continuously, but maybe applied in a pulsating manner. The intermediate electrode 106 is most preferably a GND electrode. An alternating current voltage may be preferably applied between the counter electrode 107 and the intermediate electrode 106. A pulse voltage may be applied between the counter electrode 107 and the intermediate electrode 106.

The counter electrode 107 is preferably cooled to no higher than the dew-point temperature of the water vapor 201. It is preferred that the counter electrode 107 is cooled by the second cooling part 108. It is preferred that the electric-charged fine particles 205 are condensed into the second condensate liquid 206 in the outer peripheral surface of the counter electrode 107. In the initial stage of the step (e), the second condensate liquid 206 preferably forms droplets on the outer peripheral surface of the counter electrode 107. In the stage of progress of the step (e), the outer peripheral surface of the counter electrode 107 is preferably covered by the second condensate liquid 206. The counter electrode 107 preferably has a needle-like shape. The second condensate liquid 206 is preferably recovered at the tip of the counter electrode 107. The outer peripheral surface of the counter electrode 107 is preferably hydrophilic, but may be water-repellent.

The second condensate liquid 206 is preferably moved to the tip of the counter electrode 107. The second condensate liquid 206 is preferably moved to the tip of the counter electrode 107 by gravity. In order to move the second condensate liquid 206 by gravity, the counter electrode 107 is preferably oriented downward. The second condensate liquid 206 maybe moved to the tip of the counter electrode 107 by electrostatic force. The second condensate liquid 206 may be moved to the tip of the counter electrode 107 by surface tension. The second condensate liquid 206 may be moved to the tip of the counter electrode 107 by capillarity.

The amount of the second condensate liquid 206 is not less than 1 pL and not greater than 1 mL. In light of reducing analysis time, the amount of the second condensate liquid 206 is preferably not less than 100 nL and not greater than 10 µL. The amount of the second condensate liquid 206 is more preferably not less than 0.5 µL and not greater than 2 µL.

In the step (e), as shown in FIG. 6(A), it is also preferred that the second condensate liquid 206 be recovered at the tip of the counter electrode 107 by an electrostatic force. The tip of the counter electrode 107 preferably has a shape suited for concentration of the electric field, and most preferably has a needle-like shape. The second condensate liquid preferably contains a polar organic compound or water.

It is preferred that the counter electrode 107 be electrically neutralized. The electrical neutralization of the counter electrode 107 may be carried out either constantly or in an appropriate manner. The electrical neutralization of the counter electrode 107 is preferably carried out by grounding, or may be carried out by using an ionizer.

After the voltage is applied to the counter electrode 107 with respect to the intermediate electrode 106, it is most preferred that t the counter electrode 107 be cooled. Concurrently to the application of the voltage to the counter electrode 107 with respect to the intermediate electrode 106, the counter electrode 107 may be cooled. The gas sample 203 may be condensed by the counter electrode 107.

Interfering substances contained in the second condensate liquid 206 may be eliminated. The interfering substances contained in the second condensate liquid 206 may be the water vapor 201 or a substance other than the subject substance of detection. The interruption substances contained in the second condensate liquid 206 may be eliminated by a filter or an adsorbent. Alternatively, other elimination method may be also employed.

In the step (e), the step (b) is preferably continued. In the step (e), the step (c) is preferably continued. In the step (e), the step (d) is preferably continued.

<Step (f)>

In the step (f), the liquid detector 111 detects that the second condensate liquid 206 has not less than a predetermined amount. FIG. 6(B) shows the step (f). In FIG. 6(B), the liquid detector 111 is described as an optical detector. The liquid detector 111 includes a light-emitting part 111a and a light-receiving part 111b.

A variation of the amount of the light which penetrates the second condensate liquid 206 is most preferably detected by the liquid detector 111. A variation of the amount of the light which reflects the second condensate liquid 206 is preferably detected by the liquid detector 111. A variation of the amount of the light which scatters the second condensate liquid 206 is preferably detected by the liquid detector 111.

In order to prevent the liquid detector 111 from being contaminated, the liquid detector 111 preferably fails to be contact with the second condensate liquid 206; however, the liquid detector 111 may be contact with the second condensate liquid 206. The distance between the light-emitting part 111a and the light-receiving part 111b is preferably not less than 2 mm and not more than 50 mm.

The step (f) is performed in parallel to the step (e). The step (f) is performed continuously in parallel to the step (e). The step (f) may be performed intermittently in parallel to the step (e).

After the liquid detector 111 detects that the second condensate liquid 206 has not less than a predetermined amount, the step (e) is preferably stopped. After the liquid detector 111 detects that the second condensate liquid 206 has is not less than a predetermined amount, the voltage application to the counter electrode 107 is preferably stopped.

<Step (g)>

In the step (g), the support 110 is inserted into the vessel 101. The support 110 is inserted into the vessel 101 so that the detecting electrode 109 is brought into contact with the second condensate liquid 206. FIG. 7(A) shows the step (g).

It is preferred that the support 110 is moved so that the detecting electrode 109 is located immediately below the counter electrode 107. The support 110 is preferably moved straightly along the horizontal direction thereof.

The support 110 is most preferably moved automatically. The support may be moved manually or semi-automatically.

The vessel 101 preferably comprises a driving part to move the support 110. The driving part may be an electric magnet, a motor, a plunger, a spring, an air piston, or a roller. It is preferred that the moving amount of the detecting electrode 109 is controlled by a stepping motor or a stopper.

It is preferred that the step (g) is begun after the step (f) is stopped. In order to prevent the detecting electrode 109 from being destroyed electrically, it is preferred that the step (g) is begun after the voltage application to the counter electrode 107 is stopped.

In the step (g), it is preferred that the support 110 is moved on the basis of a signal from the liquid detector 111. The analyzing device 110 preferably comprises a mechanism to move the support 110 on the basis of the signal from the liquid detector 111.

In the step (g), it is preferred that the temperature of the detecting electrode 109 is identical to the temperature of the counter electrode 107. It is preferred that the temperature of the detecting electrode 109 is lower than the temperature of the counter electrode 107. It is preferred that the temperature of the detecting electrode 109 is not less than 0 degree Celsius and not greater than 20 degree Celsius. The temperature of the detecting electrode 109 is not less than 0 degree Celsius to prevent the second condensate liquid 206 from being frozen.

<Step (h)>

In the step (h), the chemical substance 202 contained in the second condensate liquid 206 is detected or quantified with the detecting electrode 109. FIG. 7(B) shows the step (h). In the step (h), it is important that the detecting electrode 109 is brought into contact with the counter electrode 107 in such a manner that the second condensate liquid 206 is interposed therebetween.

Figure 8:
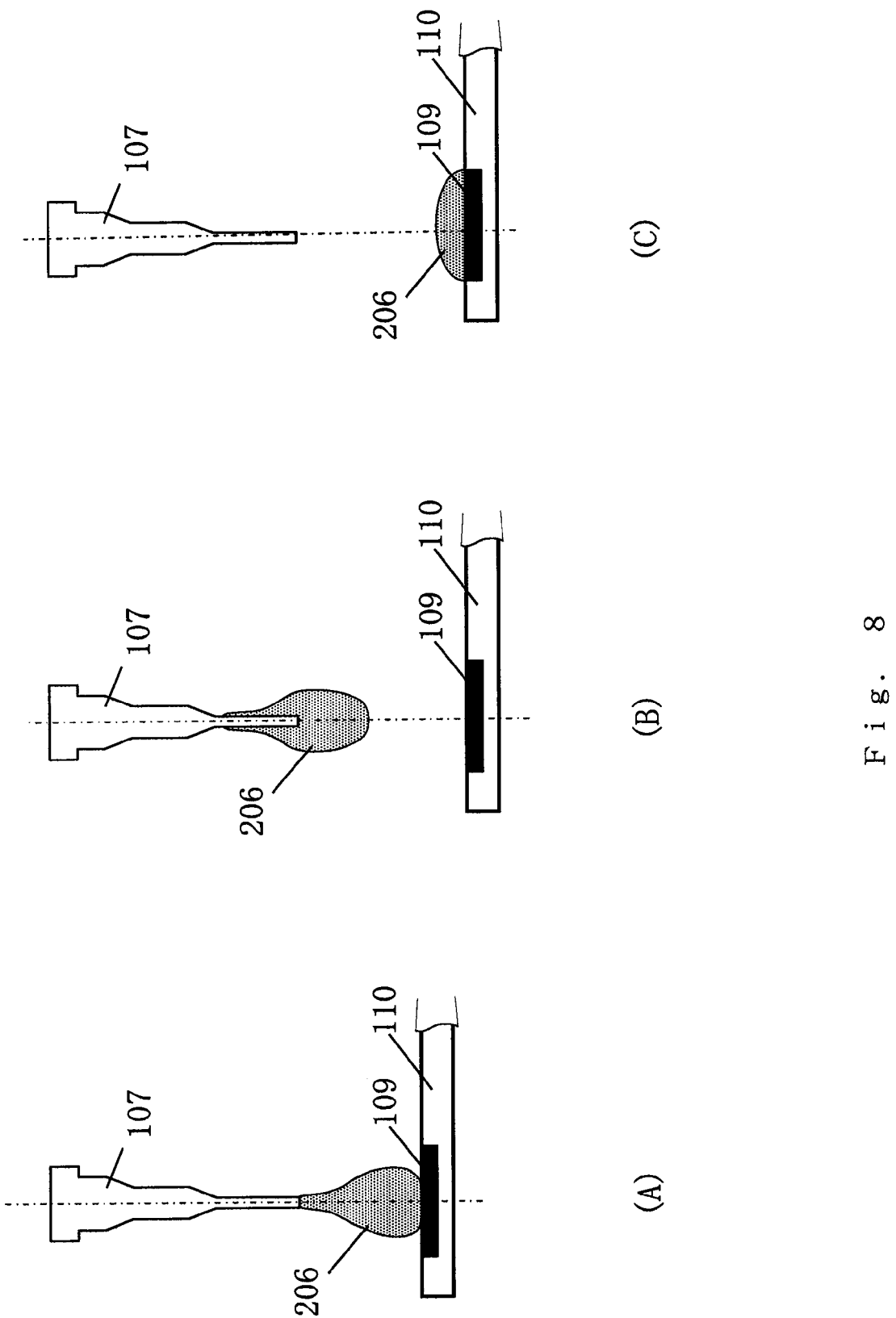
FIG. 8(A) to 8(C) show schematic views in the neighborhood of the counter electrode 107 and the detecting electrode 109 in the step (h).
Figure 9:
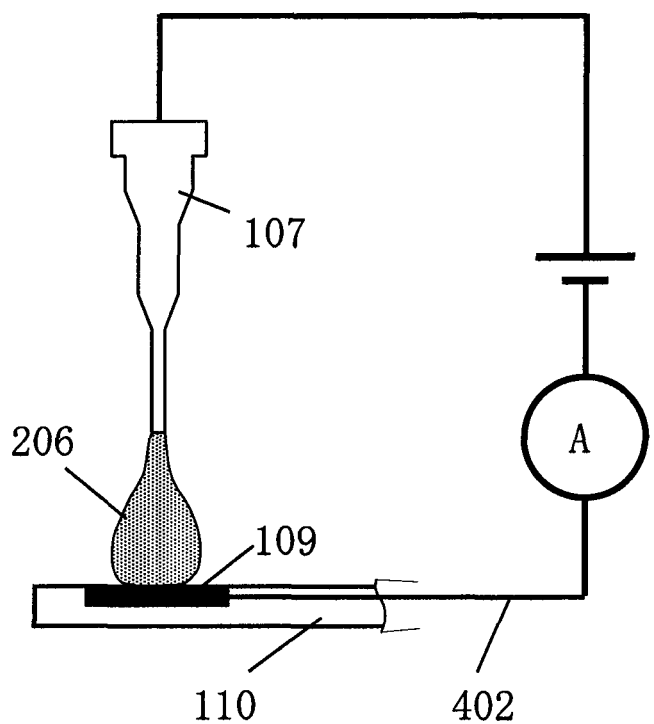
FIG. 9 shows a conceptual view representing a closed circuit formed from the counter electrode 107 to the detecting electrode 109 through the second condensate liquid 206.

FIG. 8(A) to FIG. 8(C) show schematic views in the neighborhood of the counter electrode 107 and the detecting electrode 109 in the step (h). As shown in FIG. 8(A), in the step (h), it is necessary that the second condensate liquid 206 is contact with the counter electrode 107 and the detecting electrode 109. The direct voltage is applied between the detecting electrode 109 and the counter electrode 107 to form a closed circuit between the second condensate liquid 206 and the detecting electrode 109. Since a current value is varied depending on the amount of the chemical substance contained in the second condensate liquid 206, the amount of the chemical substance contained in the second condensate liquid 206 can be measured on the basis of the current value measured by an ammeter.

As shown in FIG. 8(B) and FIG. 8(C), when the detecting electrode 109 fails to be contact with the counter electrode 107 in such a manner that the second condensate liquid 206 is interposed therebetween, the step (h) fails to be performed, since the closed circuit fails to be formed by the counter electrode 107, the second condensate liquid 206, and the detecting electrode 109.

It is preferred that one kind of the chemical substance 202 is detected with the detecting electrode 109. It is also preferred that two kinds of the chemical substance 202 are detected. The chemical substance 202 may be quantified with the detecting electrode 109. The existence of the chemical substance 202 may be detected with the detecting electrode 109. It is preferred that the step (g) and the step (h) are performed after the liquid detector 111 detects that the second condensate liquid 206 has not less than a predetermined amount. This reason is that the wasted amount of the second condensate liquid 206 is lowered.

In the step (h), it is preferred that the step (b) to step (g) are stopped.

In the step (h), it is preferred that the temperature of the detecting electrode 109 is identical to the temperature of the counter electrode 107. It is preferred that the temperature of the detecting electrode 109 is lower than the temperature of the counter electrode 107. It is preferred that the temperature of the detecting electrode 109 is not less than 0 degree Celsius and not greater than 20 degree Celsius in the step (h). The temperature of the detecting electrode 109 is not less than 0 degree Celsius to prevent the second condensate liquid 206 from being frozen.

The temperature of the detecting electrode 109 may be higher than the temperature of the counter electrode 107.

It is most preferred that the temperature of the counter electrode 107 is not less than 0 degree Celsius and not greater than 20 degree Celsius in the step (h). The temperature of the counter electrode 107 maybe not more than 0 degree Celsius as long as the second condensate liquid 206 fails to be frozen.

In the step (h), the electric potential of the counter electrode 107 is identical to the electric potential of the detecting electrode 109. It is preferred that the number of the detecting electrode 109 is reduced by causing the potential of the counter electrode 107 to agree with the potential of the detecting electrode 109. The counter electrode is preferably an electrochemical electrode.

In the embodiment of the present invention, at least two steps of from the step (b) to the step (h) may be concurrently carried out. More specifically, for example, the step (b) and the step (c) maybe carried out concurrently.

Embodiment 2

Figure 10:
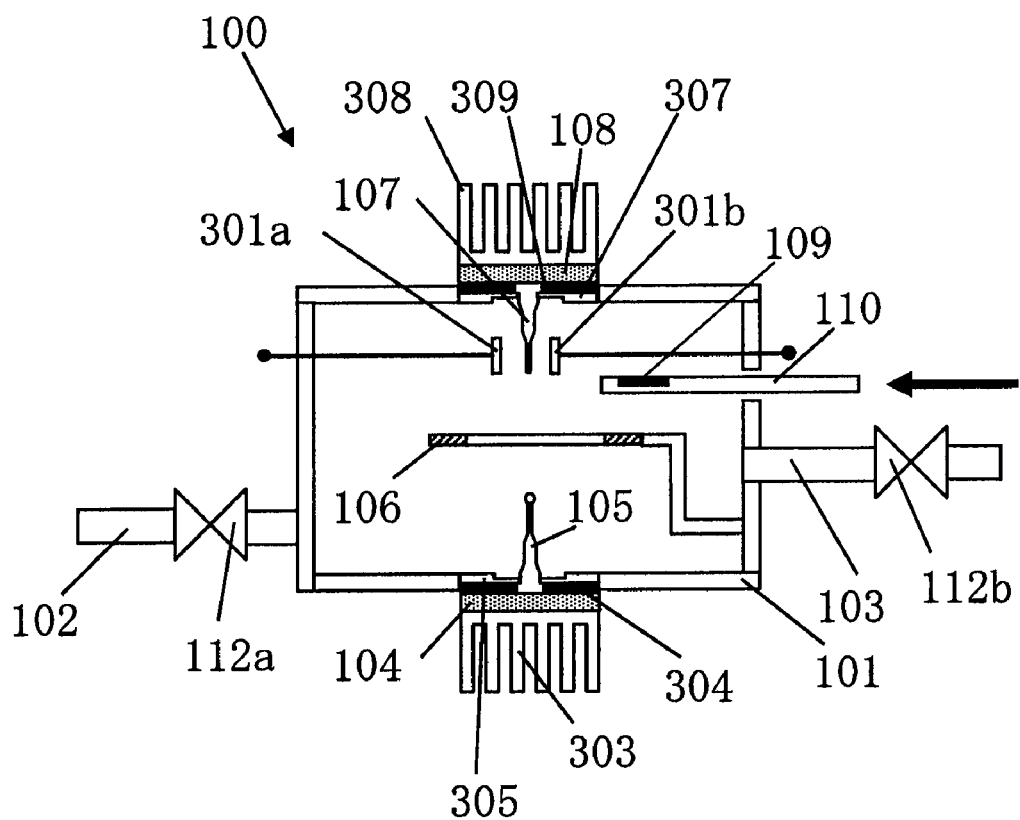
FIG. 10 shows a structural view (the step (g)) of the analyzing device according to the embodiment 2.
Figure 11:
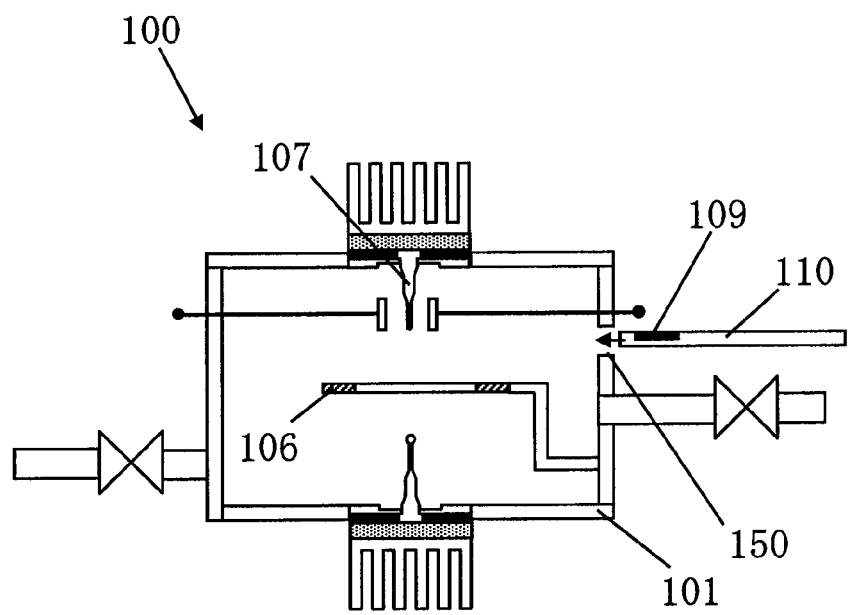
FIG. 11 shows a structural view (the step (a) to the step (f)) of the analyzing device according to the embodiment 2.
Figure 12:
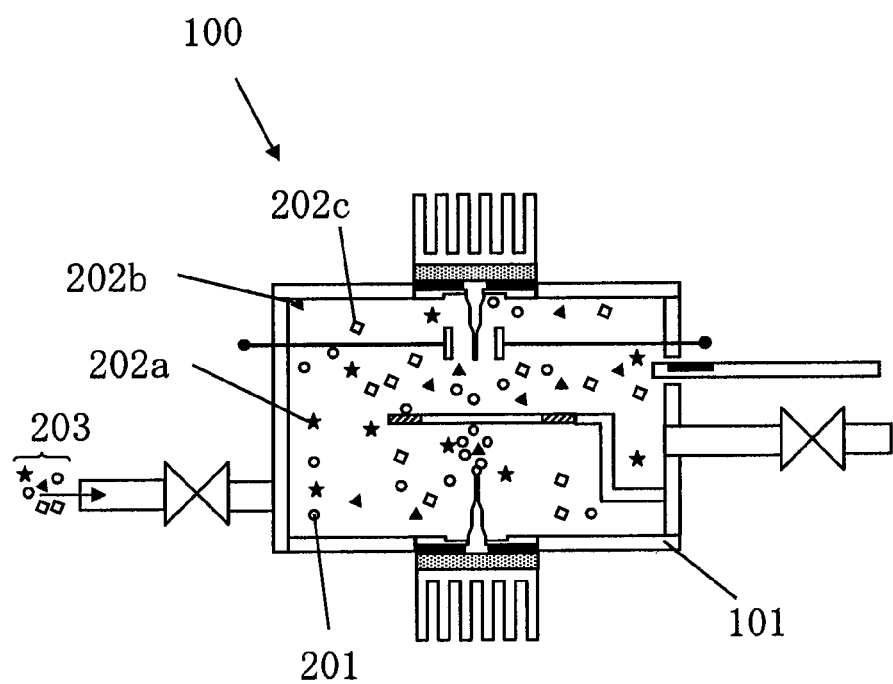
FIG. 12 shows an explanatory drawing of the step (b) according to the embodiment 2.
Figure 13:
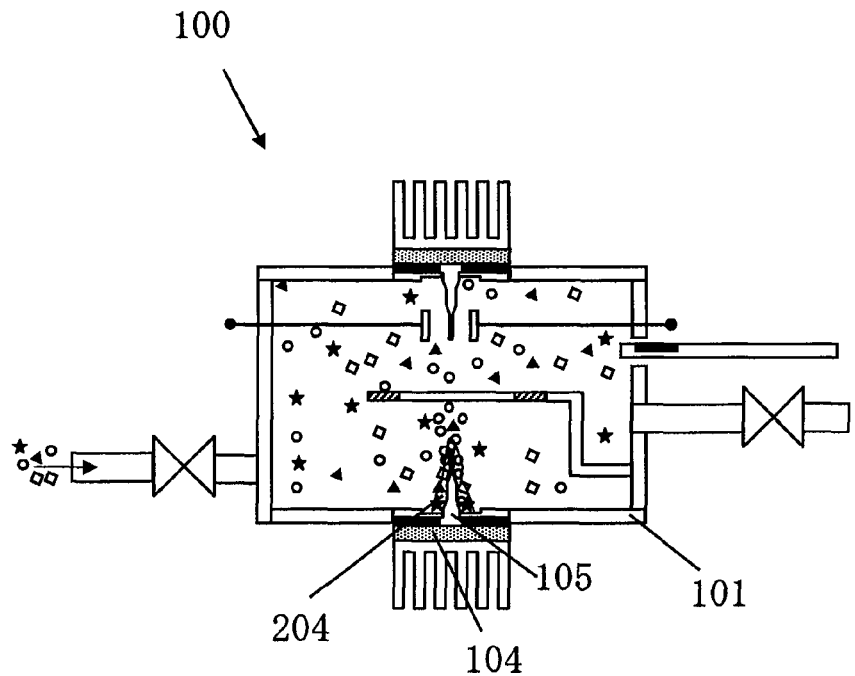
FIG. 13(A) shows an explanatory drawing of the step (c) according to the embodiment 2.
FIG. 13(B) shows an explanatory drawing of the step (d) according to the embodiment 2.
Figure 13:
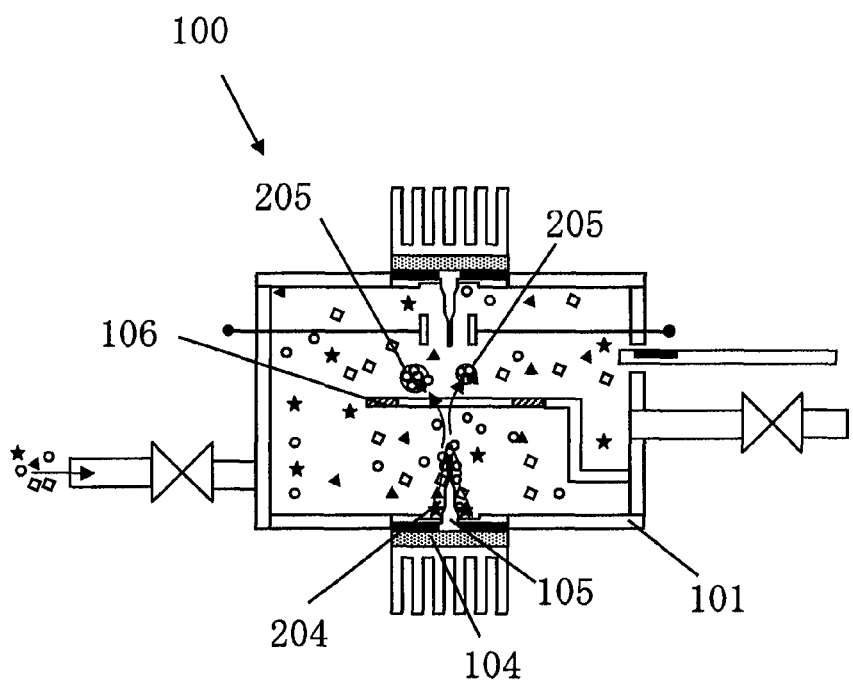
Figure 14:
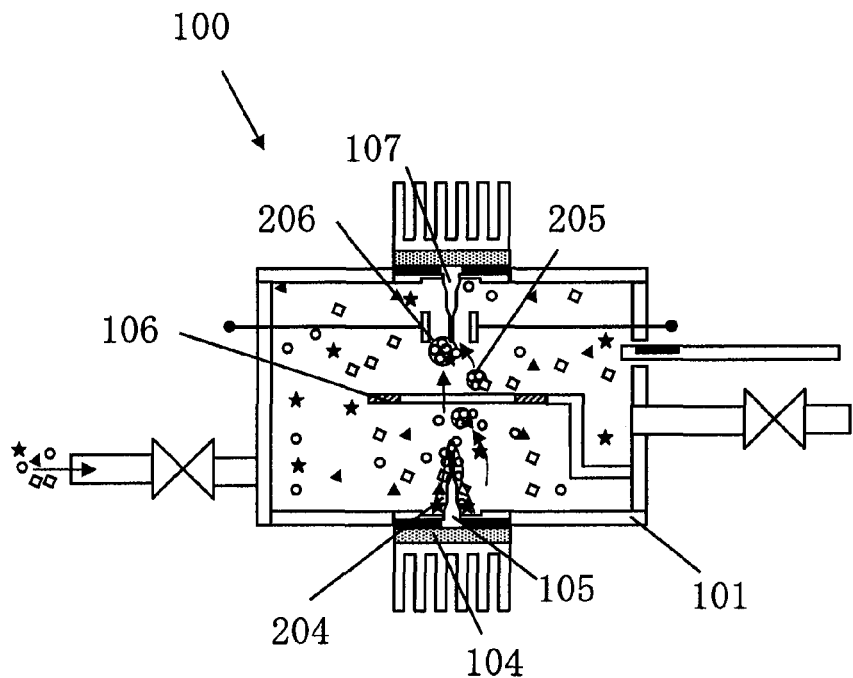
FIG. 14(A) shows an explanatory drawing of the step (e) according to the embodiment 2.
FIG. 14(B) shows an explanatory drawing of the step (f) according to the embodiment 2.
Figure 14:
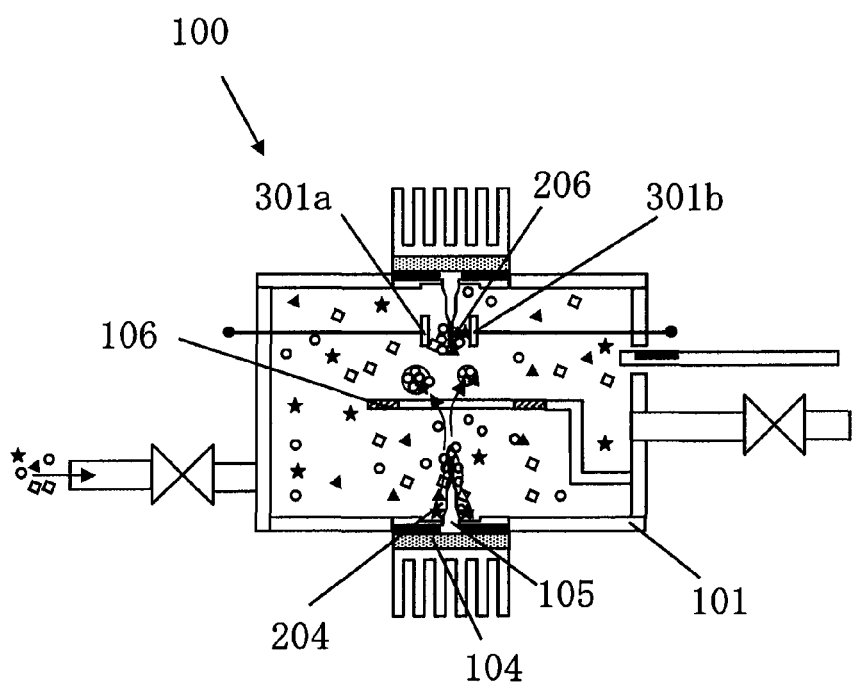
Figure 15:
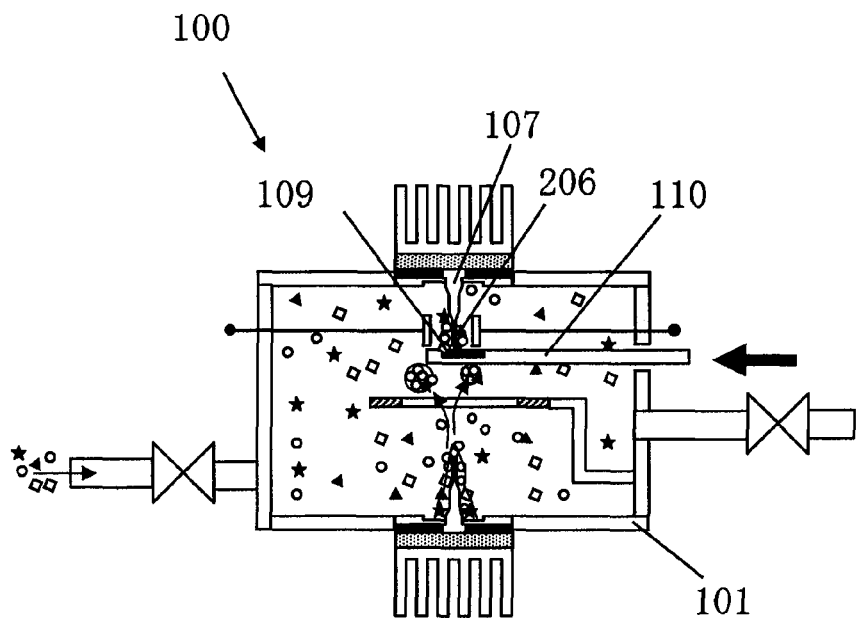
FIG. 15(A) shows an explanatory drawing of the step (g) according to the embodiment 2.
FIG. 15(B) shows an explanatory drawing of the step (h) according to the embodiment 2.
Figure 15:
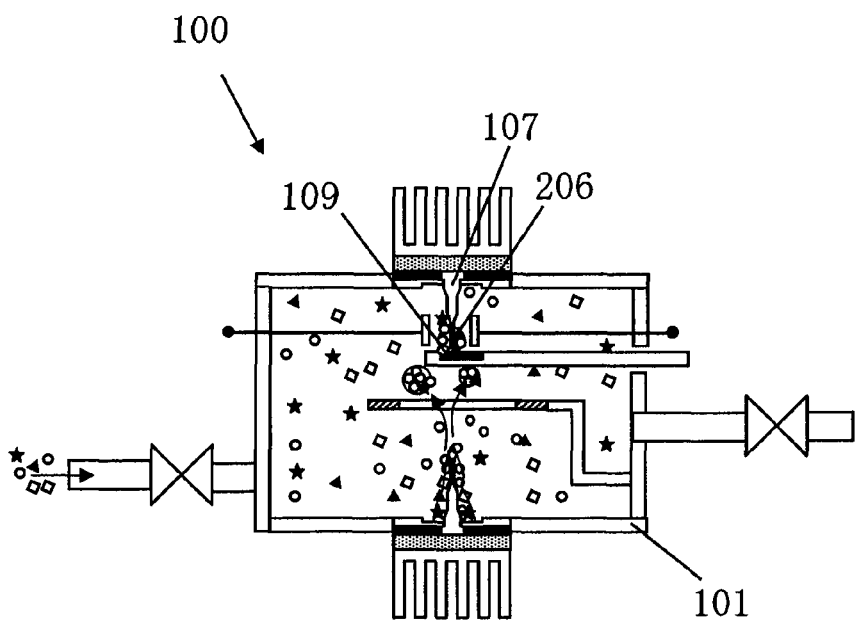

FIG. 10 and FIG. 11 show schematic views illustrating an analyzing device 100 according to Embodiment 2 of the present invention. FIG. 10 shows the condition in the step (g), and FIG. 11 shows the condition in the steps (a) to (f). In FIG.

10 and FIG. 11, the same reference numerals are given to the identical constitutive elements to those in FIG. 1, and their explanation is omitted.

The largest difference between the present Embodiment and Embodiment 1 lies in the substitution of the liquid detecting part with the electric detector. The substitution of the liquid detecting part with the electric detector allows the analyzing device 100 to be smaller. In FIG. 10, the liquid detector is represented by rectangles 301a and 302b, which mean electric detectors.

An electric detector is provided as the liquid detector in the neighborhood of the counter electrode 107. It is preferred that the liquid detector is provided in the neighborhood of the tip of the counter electrode 107. The liquid detector is preferably provided in the vessel 101. The liquid detector may be provided out of the vessel 101. It is preferred that the distance between the counter electrode 107 and the liquid detector (the electrode 301a and 302b in FIG. 10) is not less than 1 mm and not greater than 50 mm. It is more preferred that the distance between the counter electrode 107 and the liquid detector is not less than 1 mm and not more than 2 mm.

Because of the downsizing of the detector, the liquid detector is preferably the electric detector. It is preferred that the liquid detector is composed of one electrode. The liquid detector may be composed of not less than two electrodes. The liquid detector shown in FIG. 10 is composed of two electrodes 301a and 301b. It is preferred that the liquid detector detects the second condensate liquid 206 with the current flowing between the electrode 301a and the electrode 301b. It is preferred that the liquid detector is current-detecting type, potential-detecting type, capacitance-detecting type, or conductance-detecting type. It is preferred that the liquid detector is combined with the counter electrode 107. The liquid detector may detect the current flowing between the liquid detector and the counter electrode 107. The liquid detector may detect with direct current, alternate current, or pulse current.

It is preferred that the material of the electrode 301a and 301b is metal. It is preferred that the material of the electrode 301a and 301b is simple metal such as gold, silver, platinum, copper, or aluminum. The material of the electrode 301a and 301b may be alloy such as Mo—Al or copper-tungsten. It is preferred that the electrode 301a and 301b is a silver-silver chloride electrode. It is preferred that the material of the electrode 301a and 301b is inorganic material such as carbon or semiconductor. It is preferred that the electrode 301a and 301b is a MOS-transistor. The material of the electrode 301a and 301b maybe same or different. The material of the electrode 301a and 301b may be one kind of material, or two or more kinds of materials.

The shape of the electrode 301a and 301b is a wire, a plate, or a bulk. The shape of the surface of the electrode 301a and 301b may be flat or may have concave-convex structure. The shape of the electrode 301a and 301b may be same or different. The surface of the electrode 301a and 301b is preferably hydrophilic; however, it may be hydrophobic. The electrode 301a and 301b is preferably formed on a substrate.

A known liquid detection technique may be used for the liquid detector.

The cooling part 104 is preferably provided with a heat radiation part 303. When a thermoelectric element is used as the cooling part 104, the back of the cooling face is a heat generation face. The heat radiation part 303 is used for releasing the heat from the heat generation face. By releasing the heat from the heat generation face, thermoelectric element can be efficiently operated. The heat radiation part 303 is preferably a fin, and more preferably the fin is attached to a cooling fan. Alternatively, the heat radiation part 303 may be a water cooling mechanism. The heat radiation part 303 is preferably formed from a material having a thermal conductivity. The material of the heat radiation part 303 may be preferably a metal or a semiconductor.

The cooling part 104 is preferably provided with a thermal protection part 304. By providing thermal protection part 304, sites other than the atomizing electrode 105 are not cooled. The material of thermal protection part 304 preferably has a low thermal conductivity. The material of thermal protection part 304 is preferably a rubber, ceramic, or glass; however, an air gap is also acceptable. The content in the air gap is preferably air or nitrogen. Thermal protection part 304 is preferably a nonconductor.

In light of suppression of thermal conduction, the contact area of the atomizing electrode 105 with thermal protection part 304 is preferably small, and specifically, no less than 10 $\mu m^2$ and no greater than 10 $mm^2$.

The atomizing electrode 105 and the vessel 105 preferably interpose an insulating part 305. The insulating part 305 serves in electrically insulating the vessel 101 from the atomizing electrode 105. The material of the insulating part 305 is preferably an insulator such as Teflon (registered trademark), Delrin (registered trademark), or PEEK (registered trademark). In order to retain an excess condensate liquid, the insulating part 305 is preferably provided with a reservoir part. The reservoir part preferably has a groove structure, relief structure, concave-convex structure, or an absorber.

In the present invention, the shape, the material, and the position of the insulating part 305 are not limited. In light of suppression of thermal conduction, the contact area of the atomizing electrode 105 with the insulating part 305 is preferably small, and specifically, no less than 10 $\mu m^2$ and no greater than 10 $mm^2$. In order to suppress dew condensation of the water vapor, it is preferred to use a material having a lesser thermal conductivity for the insulating part 305, and a structure for suppressing thermal conduction is preferably provided.

The counter electrode 107 is preferably provided at the position that leads to suppression of direct condensation of the gas sample 203. The distance between the inlet 102 and the counter electrode 107 is preferably greater than the distance between the inlet 102 and the atomizing electrode 105. It is preferred that the intermediate electrode 106 is disposed between the atomizing electrode 105 and the counter electrode 107. It is preferred that the distance between the intermediate electrode and the atomizing electrode 105 is identical to the distance between the intermediate electrode 106 and the counter electrode 107. The distance between the intermediate electrode 106 and the atomizing electrode 105 may be greater or smaller than the distance between the intermediate electrode 106 and the counter electrode 107.

The counter electrode 107 is preferably provided with a second insulation part 307. The insulation part 305 serves in electrically insulating the vessel 101 from the counter electrode 107. The material of the second insulation part 307 is preferably an insulator such as Teflon (registered trademark), Delrin (registered trademark), or PEEK (registered trademark). In order to retain an excess condensate liquid, the second insulation part 307 is preferably provided with a reservoir part. The reservoir part preferably has a groove structure, relief structure, concave-convex structure, or an absorber. In the present invention, the shape, the material and the position of the second insulation part 307 are not limited. In light of suppression of thermal conduction, the contact area of the counter electrode 107 with the second insulation part 307 is preferably small, and specifically, no less than 10 $\mu m^2$ and no greater than 10 $mm^2$.

The second cooling part 108 is preferably provided with a second heat radiation part 308. When a thermoelectric element is used as the second cooling part 108, the back of the cooling face is a heat generation face. The second heat radiation part 308 is used for releasing the heat from the heat generation face. By releasing the heat from the heat generation face, thermoelectric element can be efficiently operated. The second heat radiation part 308 is preferably a fin, and more preferably the finis attached to a cooling fan. Alternatively, the second heat radiation part 308 maybe a water cooling mechanism. The second heat radiation part 308 is preferably formed from a material having a thermal conductivity. The material of the second heat radiation part 308 may be preferably a metal or a semiconductor.

The second heat radiation part 308 is preferably provided with a second thermal protection part 309. By providing the second thermal protection part 309, sites other than the counter electrode 107 are not cooled. The material of the second thermal protection part 309 preferably has a low thermal conductivity. The material of the second thermal protection part 309 is preferably a rubber, ceramic, or glass; however, an air gap is also acceptable. The content in the air gap is preferably air or nitrogen.

In light of suppression of thermal conduction, the contact area of the counter electrode 107 with the second thermal protection part 309 is preferably small, and specifically, no less than 10 $\mu m^2$ and no greater than 10 $mm^2$.

FIG. 12 to FIG. 15 show explanatory views of the chemical substance analyzing method according to Embodiment 2. In FIG. 12 to FIG. 15, the same reference numerals are given to the identical constitutive elements to those in FIG. 10, and their explanation is omitted.

The largest difference between the present embodiment and the embodiment 1 is the step (e). The difference is described below.

In the step (e), the liquid detector detects that the electric-charged fine particles 205 is configured to be the second condensate liquid 206 at a constant amount which is not less than a predetermined amount. FIG. 14(B) shows the step (e). In FIG. 14(B), the liquid detector is described as an electric detector. The liquid detector comprises an electrode 301a and an electrode 301b.

It is most preferred that the liquid detector detects the second condensate liquid 206 with the current flowing between the electrode 301a and the electrode 301b.

In the step (e), in order to prevent the liquid detector (the electrode 301a and the electrode 301b) from being contaminated, the contact area of the liquid detector with the second condensate liquid 206 is not less than 100 $\mu m^2$ and not greater than 1 $mm^2$. The distance between the electrode 301a and the electrode 301b is not less than 2 mm and not greater than 50 mm.

The step (f) is preferably performed in parallel to the step (e). The step (f) is preferably performed continuously in parallel to the step (e). The step (f) may be performed intermittently in parallel to the step (e).

Similarly to the embodiment 1, in the step (e), the liquid detector (the electrode 301a and the electrode 301b) detects that the second condensate liquid 206 has is not less than a predetermined amount.

After the liquid detector (the electrode 301a and the electrode 301b) detects that the second condensate liquid 206 has not less than a predetermined amount, the step (e) is preferably stopped. After the liquid detector (the electrode 301a and the electrode 301b) detects that the second condensate liquid 206 has not less than a predetermined amount, the voltage application to the counter electrode 107 is preferably stopped.

In the present embodiment, any of at least two steps of the step (b) to the step (h) may be performed at the same time. For example, the step (b) and the step (c) may be performed at the same time, or each of the steps may be performed in an orderly sequence.

The electric-charged fine particles 205 may be heated in the present Embodiment. The concentration of the chemical substance 202 may be increased by heating the electric-charged fine particles 205. For heating the electric-charged fine particles 205, infrared light is preferably used. When the electric-charged fine particles 205 are heated with infrared light, it is preferred that a wavelength of the absorption peak of water is used. The infrared light for use in heating the electric-charged fine particles 205 is preferably not irradiated on the atomizing electrode 105 and the counter electrode 107. The infrared light for use in heating the electric-charged fine particles 205 is preferably focused. It is also preferred that the infrared light for use in heating the electric-charged fine particles 205 be wave guided in the vessel 101. In such a case, an optical waveguide is preferably provided in the vessel 101. It is also preferred that a window of infrared light be provided in a part of the vessel 101. A heater may be also used for heating the electric-charged fine particles 205.

In the step (d), corona discharge may be used, but electrostatic spraying is most preferably used. However, when relative humidity in the gas sample 203 is too low, or when sufficient first condensate liquid 204 is not produced on the outer peripheral surface of the atomizing electrode 105, the electrostatic spraying may be accompanied by the corona discharge. Accordingly, the electric-charged fine particle production method in the step (d) is not limited to the electrostatic spraying in the present invention.

In the step (d) of the present embodiment, application of the voltage between the atomizing electrode 105 and the intermediate electrode 106 is preferably regulated depending on the electric current that flows between the atomizing electrode 105 and the intermediate 106. When an electric current with no less than the threshold value flows between the atomizing electrode 105 and the intermediate electrode 106, application of the voltage between the atomizing electrode 105 and the intermediate electrode 106 is preferably interrupted; however, merely reducing the applied voltage is also acceptable. In addition, when the electric current that flows between the atomizing electrode 105 and the intermediate electrode 106 becomes no greater than the threshold value, the application of the voltage may be resumed.

In order to remove the water vapor 201 and the chemical substance 202 from the atomizing electrode 105 after detection of the chemical substance, the atomizing electrode 105 is preferably heated. When the atomizing electrode 105 is heated, a clean gas is preferably injected into the vessel 101. It is preferred that the clean gas does not contain the water vapor 201 or chemical substance 202.

To remove the water vapor 201 and the chemical substance 202 by heating the atomizing electrode 105, it is preferred that a thermoelectric element is used. Thermoelectric element is preferably the cooling part 104. Use of thermoelectric element is convenient since the cooling face and the heating face can be easily inverted. Use of an identical thermoelectric element for the condensation step and for removing the water vapor 201 and the chemical substance 202 may be responsible for miniaturization of the apparatus for analysis. For detecting removal of the water vapor 201 and the chemical substance 202, the detecting electrode 109 may be used; however, an electrode other than the detecting electrode 109 may be used.

In order to remove the water vapor 201 and chemical substance 202 from the intermediate electrode 106 after detection of the chemical substance, it is also preferred that the counter electrode 106 is heated in the present embodiment. When the counter electrode 106 is heated, a clean gas is preferably injected into the vessel 101. It is preferred that the clean gas does not contain the water vapor 201 or the chemical substance 202.

For heating the intermediate electrode 106, it is preferred that a thermoelectric element is used. Use of thermoelectric element is convenient since the cooling face and the heating face can be easily inverted. For detecting removal of the water vapor 201 and the chemical substance 202, the detecting electrode 109 may be used; however, an electrode other than the detecting electrode 109 maybe used.

In order to remove the water vapor 201 and the chemical substance 202 from the counter electrode 107 after detection of the chemical substance, it is preferred to heat the counter electrode 107 in the present embodiment. When the counter electrode 107 is heated, a clean gas is preferably injected into the vessel 101. It is preferred that the clean gas does not contain the water vapor 201 or chemical substance 202.

For heating the counter electrode 107, it is preferred that a thermoelectric element is used. Thermoelectric element is preferably the second cooling part 108. Use of thermoelectric element is convenient since the cooling face and the heating face can be easily inverted. Use of an identical thermoelectric element for the step (e) and for removing the water vapor 201 and the chemical substance 202 maybe responsible for miniaturization of the apparatus for analysis. For detecting removal of the water vapor 201 and the chemical substance 202, the detecting electrode 109 may be used; however, an electrode other than the detecting electrode 109 may be used.

It is preferred that the chemical substance which is a diagnostic marker is examined using the chemical substance analyzing method according to the present embodiment. The diagnostic marker is preferably a diagnostic marker for diabetes. The diagnostic marker may be a diagnostic marker for cancer, allergy, infection disease, lifestyle diseases, asthma, liver ailment, or kidney disease.

It is preferred that the analyzing device 100 is a device for examining a diagnostic marker. It is preferred that the device for examining a diagnostic marker is device for examining a diagnostic marker for diabetes. The device for examining a diagnostic marker may be a device for examining a diagnostic marker for cancer, allergy, infection disease, lifestyle diseases, asthma, liver ailment, or kidney disease.

Embodiment 3

Figure 16:
FIG. 16 shows a perspective view of the detecting electrode according to the embodiment 3.
Figure 17:
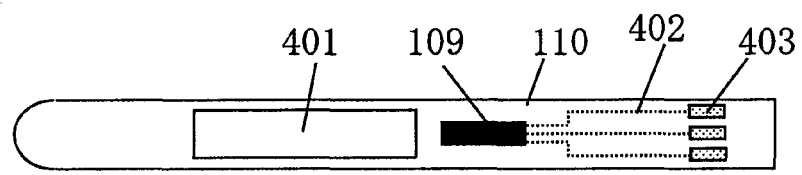
FIG. 17 shows a top view of the detecting electrode in FIG. 16.
Figure 18:
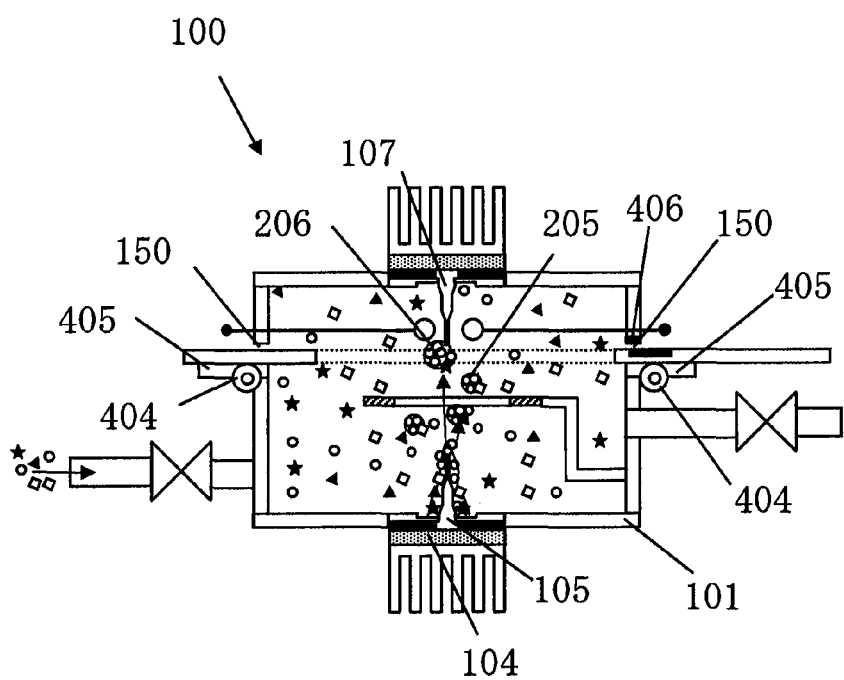
FIG. 18 shows a structural view of the analyzing device according to the embodiment 3.

FIG. 16 and FIG. 17 show perspective views and a plan view of the detecting electrode 109 according to the embodiment 3 of the present invention. In FIG. 16 and FIG. 17, the same reference numerals are given to the identical constitutive elements to those in FIG. 3, and their explanation is omitted. FIG. 18 shows a chemical substance analyzing device according to the embodiment 3 of the present invention. In FIG. 18, the same reference numerals are given to the identical constitutive elements to those in FIG. 1, and their explanation is omitted.

The largest difference between the present embodiment and the embodiment 1 lies in that the number of the region of contact of the vessel 101 with the support 110 is two. In FIG. 18, the vessel 101 is in contact with the support 110 in the left and right sides of the vessel 101. In FIG. 18, the vessel 101 is preferably in contact with the support 110 via a mounting mechanism 150.

The difference between the present embodiment and the embodiment 1 lies in that a through-hole 401 is provided with the support 110, as shown in FIG. 16 and FIG. 17. By providing the through-hole 401 with the support 110, it can be suppressed that the electric-charged fine particles 205 adhere to the support 110.

The difference between the present embodiment and the embodiment 1 lies in that a driving section 401 is provided with the vessel 101, as shown in FIG. 18. By providing the driving part 404 with the vessel 101, the support 110 moves with ease.

It is most preferred that the number of the region of contact of the vessel 101 with the support 110 is two. The number of the region of contact of the vessel 101 with the support 110 may be three or more. It is most preferred that the region of contact of the vessel 101 with the support 110 is flat. The shape of the region of contact of the vessel 101 with the support 110 maybe curved surface, straight line, or curved line. The contact area of the support 110 with the vessel 101 is preferably not less than 10 square micrometers and not more than 100 square millimeters.

The through-hole 401 is provided with the support 110. It is preferred that the area of the portion of the support 110 which intersects with the imaginary line between the atomizing electrode 105 and the counter electrode 107 is smaller by providing the through-hole 401 with the support 110. It is preferred that the shape of the through-hole 401 is rectangular. The through-hole 401 may be circular, trapezoidal, square, elliptical, or polygonal. The cross-sectional area of the through-hole 401 is not less than 100 square micrometers and not more than 10 square millimeters. The number of the through-hole 401 may be one or more. A structure which decreases in the area of the support 110 may be provided.

It is preferred that the driving part 404 is provided with the mounting mechanism 150. It is preferred that the driving part 404 is used for moving the support 110. The driving part 404 is provided at the end of the mounting mechanism 150. It is preferred that the driving part 404 is an electric magnet, a motor, a plunger, a spring, an air piston, or a roller. The driving part 404 is preferably in contact with the bottom surface of the support 110. The driving part 404 may be in contact with the side of the support 110. It is preferred that the number of the portion where the driving part 404 is in contact with the support 110 is one. The number of the portion may be two or more. One driving part 404 is preferably provided. It is more preferred that two or more driving sections 404 are provided.

In order to support the support 110, it is preferred that a stage 405 is provided with the vessel 101. By providing the stage 405, the support 110 can move with ease since the contact area of the support 110 with the vessel 101 increases. It is most preferred that the stage 405 is provided at the end of the mounting mechanism 150. A guide is preferably provided with the stage 405. By providing the guide, the support 110 can move with ease since the movement direction of the support 110 is determined. A temperature adjuster is preferably provided with the state 405. By providing the temperature adjuster, the temperatures of the support 110 and the detecting electrode 109 can be maintained to be constant.

It is preferred that the analyzing device 100 comprises an analysis part which analyses the signal output from the detecting electrode 109. It is preferred that the analyzing device 100 comprises a display part in which the results obtained in the analysis part are displayed. It is preferred that the analyzing device 100 comprises a memory part which memorizes the results obtained in the analysis part. It is preferred that the analyzing device 100 comprises an electric source to drive the detecting electrode 109, the cooling part 104, and the driving part 404. The analyzing device 100 preferably comprises a transmission part which transmits the result from the analysis part.

It is preferred that the analyzing device 100 comprises liquid-detecting analysis part which analyses the signal output from the liquid-detecting part 111. It is preferred that the analyzing device 100 comprises a display part in which the results obtained in the liquid-detecting analysis part are displayed.

If the initial position of the detecting electrode 109 is outside the vessel 101, the support 110 may be mounted to the end of the vessel 101 prior to the step (b). After the support 110 is mounted, the support 110 preferably is moved by the driving part 404 in the step (g) to bring the detecting electrode 109 in contact with the second condensate liquid 206. The through-hole 401 may be inside the vessel 101 prior to the step (b), or may be outside the vessel 101.

If the through-hole 401 is located in the vessel 101 in the step (d), it is most preferred the through-hole 401 is located at the imaginary line between the atomizing electrode 105 and the counter electrode 107. In this case, it is most preferred that at least the portion of the electric-charged fine particles 205 are recovered into the counter electrode 107 through the through-hole 401.

If the through-hole 401 is located in the vessel 101 in the step (e), it is most preferred the through-hole 401 is located at the imaginary line between the atomizing electrode 105 and the counter electrode 107. In this case, it is most preferred that at least the portion of the electric-charged fine particles 205 are recovered into the counter electrode 107 through the through-hole 401.

In the step (g), the support 110 moves until the detecting electrode 109 comes in contact with the second condensate liquid 206. In the step (g), it is preferred that the support 110 moves in such a manner that the detecting electrode 109 is located just below the counter electrode 107. In the step (g), the support 110 is moved by the driving part 404. In the step (g), the second condensate 206 is held between the counter electrode 107 and the detecting electrode 109. Namely, as shown in FIG. 8(A), the second condensate liquid 206 is brought in contact with the counter electrode 107 and the detecting electrode 109.

It is preferred that the movement amount of the support 110 is controlled by a stepping motor or a stopper.

In the step (g), a direct current is applied in a condition where the counter electrode 107, the second condensate liquid 206, and the detecting electrode 109 are electrically connected. It is preferred that the surface of the detecting electrode 109 is located at the higher position than the surface of the support 110. It is preferred that the detecting electrode 109 has a convex with regard to the surface of the support 110. The surface of the detecting electrode 109 may be located at the lower position than the surface of the support 110. The detecting electrode 109 may has a concave with regard to the surface of the support 110.

It is preferred that the support 110 comprises a wire 402 and a pad 403 to pick up the electrical signal from the detecting electrode 109. The external surface of the wire 402 is preferably covered by an insulator. It is preferred that the wire 402 is implanted in the support 110. The wire 402 is electrically connected with the detecting electrode 109. It is preferred that the pad 403 is exposed. The pad 403 is electrically connected with the wire 402. It is preferred that the surface of the pad 403 is located at the higher position than the surface of the support 110. It is preferred that the pad 403 has a convex with regard to the surface of the support 110. The surface of the pad 403 may be located at the lower position that the surface of the support 110. The pad 403 may have a concave with regard to the surface of the support 110. The material, size, number, and position of the wire 402 and the pad 403 are not limited in the present invention.

As shown in FIG. 18, it is preferred that the vessel 101 comprises a contact point 406 to pick up the electric signal from the detecting electrode 109. It is preferred that the electrical signal output from the detecting electrode is transmitted to the analysis part via the contact point 406. The vessel 101 preferably comprises a mechanism which connects electrically with the detecting electrode 109 via the support 110. It is preferred that the vessel 101 comprises a mechanism which brings in contact physically with the detecting electrode 109 via the support 110. The vessel 101 may comprise a mechanism to pick up an optical signal from the detecting electrode 109.

After the step (h), it is preferred that the support moves to the position where the detecting electrode 109 fails to come in contact with the second condensate liquid 206. After the step (h), it is most preferred that the support 110 is removed outside the vessel 101 after the step (h). The support 110 is moved by the driving part 404.

Fourth Embodiment

Figure 19:
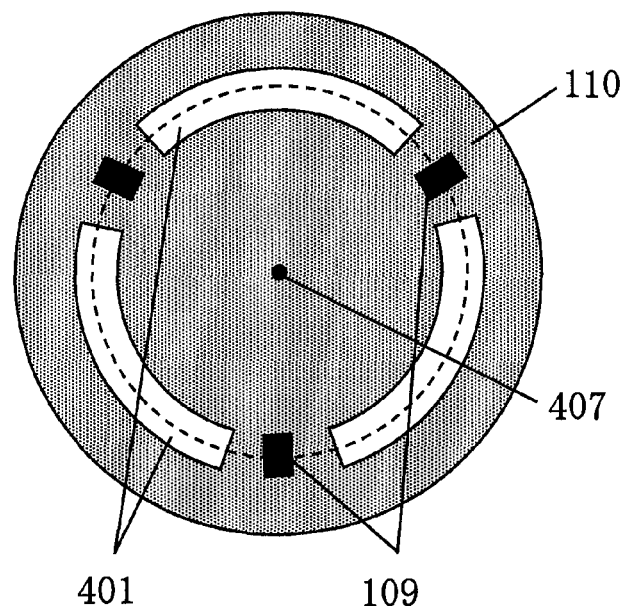
FIG. 19 shows a top view of the support provided with a plurality of the detecting electrodes according to the embodiment 4.
Figure 20:
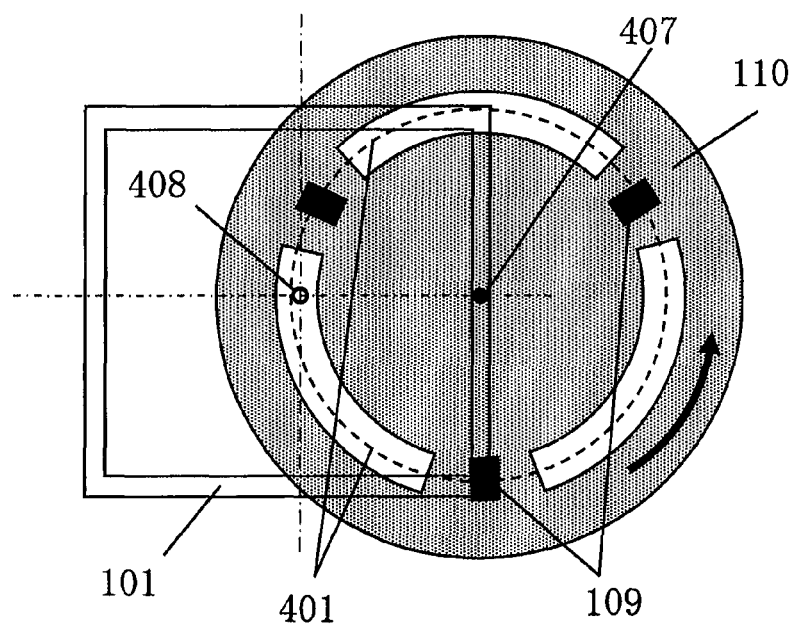
FIG. 20 shows a cross-sectional view of the analyzing device according to the embodiment 4.

FIG. 19 shows a top view of the support 110 with a plurality of the detecting electrodes 109 according to the fourth embodiment. In FIG. 19, the same reference signs are used for the same constitution elements shown in FIG. 1 to FIG. 3, and their explanation is omitted. FIG. 20 shows a cross-sectional view along the horizontal direction of the chemical substance analyzing device according to the fourth embodiment and includes a surface including the support 110. In FIG. 20, the same reference signs are used for the same constitution elements shown in FIG. 1 to FIG. 3, and their explanation is omitted.

The largest difference between the present embodiment and the embodiment 1 lies in that the support 110 is rotatable. It is preferred to rotate the support 110 around a rotation center 407. By rotating the support 110, the detecting electrode 109 provided on the support 110 can move with ease. As shown in FIG. 19, it is most preferred that the support 110 is circular. The shape of the support 110 may be polygon, trapezoid, parallelogram, rectangle, ellipse, star, or rice ball.

If the support 110 is circular, it is preferred the support 110 has a diameter of not less than 5 mm and not more than 110. In order to handle with ease, it is more preferred that the support 110 has a diameter of not less than 5 mm and not more than 20 mm.

If the support 110 is not circular, the length along the longitudinal direction of the support 110 is not less than 5 mm and not more than 100 mm. In order to handle with ease, it is more preferred that the length along the longitudinal direction of the support 110 is not less than 5 mm and not more than 20 mm.

The support 110 preferably comprises one detecting electrode 109. The support may comprise two or more detecting electrodes 109. The detecting electrodes 109 is pre ferably provided around the rotation center 407. As shown in FIG. 19, it is preferred that two or more detecting electrodes 109 is provided on the circumference around the rotation center 407. It is preferred that two or more detecting electrodes 109 is provided at the positions with an equal distance from the rotation center 407. Two or more detecting electrodes 109 is preferably provided at equal intervals; however, may be provided at different intervals. Two or more detecting electrodes 109 are identical kinds of electrodes or different kinds of electrodes.

The support 110 preferably comprises one through-hole 401. The support 110 may comprise two or more through-holes 401. The through-holes 401 are provided around the rotation center 407. As shown in FIG. 19, two or more through-holes 401 are preferably provided on the circumference around the rotation center 407. Two or more through-holes 401 are provided at the positions with an equal distance from the rotation center 407. Two or more through-holes 401 are provided at equal intervals. Two or more through-holes 401 maybe provided at different intervals. It is most preferred that the detecting electrode 109 is provided at the position interposed between the through-holes 401. It is preferred that the detecting electrodes 109 are provided alternately with the through-holes 401. Two or more through-holes 401 may have an identical size or different sizes. Two or more through-holes 401 may have an identical shape or different shapes.

It is preferred that the shape of the through-hole 401 is circular sector. The through-hole 401 maybe rectangular, circular, trapezoidal, square, elliptical, or polygonal. It is preferred that the cross-sectional area of the through hole 401 is not less than 100 square micrometers and not more than 10 square millimeters. The number of the through-hole 401 may be one, or may be two or more.

FIG. 20 shows a cross-sectional view of the chemical substance analyzing device 100. As shown in FIG. 20, it is preferred that the two or more detecting electrodes 109 are disposed on the support 110 in such a manner that they can move just below the counter electrode 408. It is preferred that the two or more through-holes 401 are disposed on the support 110 in such a manner that they can move just below the counter electrode 408. It is preferred that the two or more through-holes 401 are disposed on the support 110 in such a manner that they can move on the imaginary line between the atomizing electrode 105 and the counter electrode 408. It is most preferred that the rotation center 407 is fixed to the vessel 101. The support 110 is removable from the vessel 101.

In the step (g), the support 110 is mounted at one end of the vessel 101. It is preferred that the support 110 rotates to move the detecting electrode 109 after the support 110 is mounted to the vessel 101.

In the step (g), it is preferred that the movement amount of the detecting electrode 109, namely, the rotation amount of the circular support 110 shown in FIG. 19 and FIG. 20 is controlled by a stepping motor or a stopper.

Embodiment 5

Figure 21:
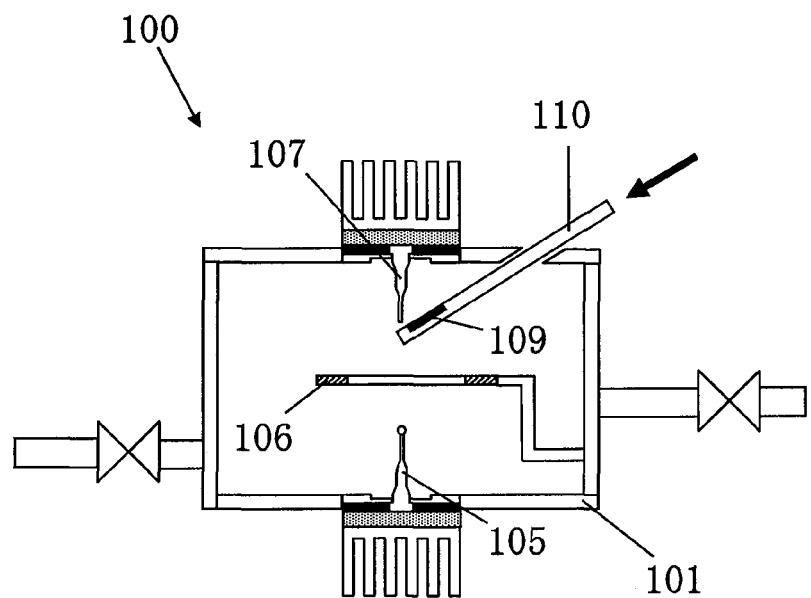
FIG. 21 shows a structural view of the analyzing device according to the embodiment 5.

FIG. 21 shows an analyzing device 100 according to the embodiment 5 of the present invention. In FIG. 21, the same reference numerals are given to the identical constitutive elements to those in FIG. 1, and their explanation is omitted.

The largest difference between the present embodiment and the embodiment 1 lies in that the angle of movement of the support 110 and the detecting electrode 109. As shown in FIG. 21, in the step (g), it is preferred that the support 110 is inserted from above the vessel 101. In FIG. 21, the liquid detecting part 111 is not shown.

Figure 22:
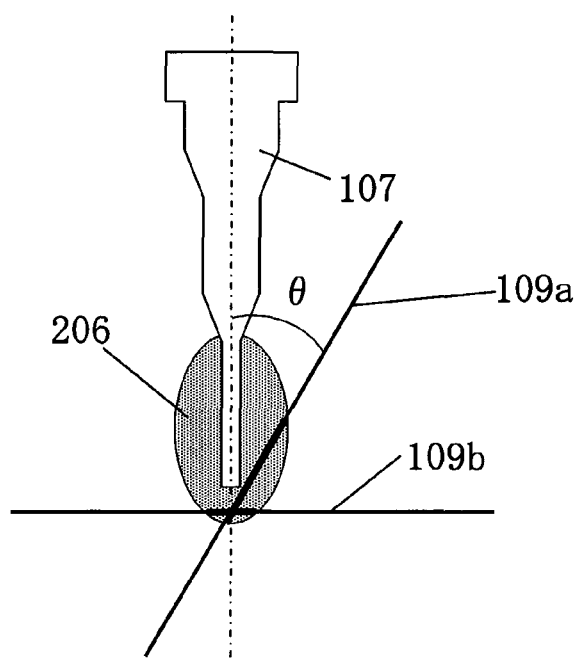
FIG. 22 shows an exploded view in the neighborhood of the counter electrode in FIG. 18.

FIG. 22 shows an exploded view in the neighborhood of the counter electrode 107 in FIG. 21. The angle theta formed by the axis direction of the counter electrode 107 and the plane direction of the detecting electrode 109 is not less than 0 degree and not more than 89 degree. It is more preferred that the angle theta is not less than 0 degree and not more than 60 degree. The detecting electrode 109a shown in FIG. 22 has the angel theta of 30 degree. The detecting electrode 109b shown in FIG. 22 has the angel theta of 90 degree. As shown in FIG. 22, the detecting electrode 109a has larger contact area with the second condensate liquid 206 than the detecting electrode 109b.

It is preferred that the liquid detecting part 111 is disposed at the position where it fails to prevent the support 110 and the detecting electrode 109 from moving. It is most preferred that the imaginary line between the light-emitting part 111a and the light-receiving part 111b is orthogonal to the movement direction of the support 110. Namely, in FIG. 22, it is most preferred that the light-emitting part 111a and the light-receiving part 111b are provided orthogonally to the plane of paper. It is preferred that the angle formed by the imaginary line between the light-emitting part 111a and the light-receiving part 111b and the movement direction of the detecting electrode 109 and the support 110 is approximately 90 degree.

Example

<Step (a)>

As an example, the chemical substance detecting device according to the embodiment 1 was formed. The vessel 101 was prepared with cutting work from an aluminum plate with a thickness of 4 millimeters. The vessel 101 was configured to be rectangular parallelepiped of 38 millimeters×38 millimeters×38 millimeters. A portion of the vessel 101 was configured to be replaceable with an acryl resin plate. Since the forming process of the condensate liquid may be observed, it was more preferred that a portion of the vessel 101 was made of transparent material. The inside wall was polished smoothly to suppress gas absorption. A portion of the vessel 101 was prepared with a PEEK plate. The intermediate electrode 106 was provided at the portion where the vessel 101 was prepared with a PEEK plate.

The inlet 102 was provided at the (lateral) end of the vessel 101. The inlet 102 was a stainless pipe with an external diameter of ⅛ inch and a length of 50 mm. The inlet 102 was disposed 10 mm away from the bottom surface of the vessel 101. The inlet 102 was provided horizontally to the bottom surface of the vessel 101.

The outlet 103 was provided at the other end (the lateral side opposite the inlet 102) of the vessel 101. The outlet 103 was a stainless pipe with an external diameter of ⅛ inch and a length of 50 mm. The outlet was disposed 4 mm away from the bottom surface of the vessel 101. The outlet 103 was provided horizontally to the bottom surface of the vessel 101.

Thermoelectric element as the cooling part 104 was provided at the end (the bottom surface) of the vessel 101. The cooling part had a size of 14 millimeters×14 millimeters×1 millimeter. The cooling part 104 had a maximum endotherm of 0.9 W and the largest temperature difference of 69 degree Celsius. Thermolysis surface of the cooling part 104 was covered with a ceramic material. Since the ceramic material had a plurality of fine convexes and concaves on the surface thereof, the object which was in contact with the ceramic material was cooled efficiently.

The heat radiation part 303 was provided with the cooling part 104. Heat radiation fins were employed as the heat radiation part 303. The heat radiation part 303 was prepared with cutting work from the aluminum. The number of the heat radiation fins was six. Each of the heat radiation fins had a size of 16 millimeters×15 millimeters×1 millimeter. A cooling fan (KD1208PTBS2-6, SUNON) was provided in the neighborhood of the heat radiation part 303 to promote heat radiation.

Thermal protection part 304 was provided between the cooling part 104 and the vessel 101. A rubber film with a thickness of 1 millimeter was employed as thermal protection part 304. A hole was provided at the portion of the rubber film to penetrate the atomizing electrode 105. The hole has a diameter of 1 millimeter.

The atomizing electrode 105 was provided at the end (top end) of the cooling part 104. The contact area of the atomizing electrode 105 and the cooling part 104 was 0.5 square millimeter. A stainless needle with provided in the vessel 101 as the atomizing electrode 105. The length of the stainless needle was 3 millimeters. The diameter at the thickest portion of the stainless needle was 0.79 millimeter. The diameter at the thinnest portion of the stainless needle was 0.5 millimeter. A sphere with a diameter of 0.72 mm was provided at the top end of the stainless needle to perform the step (d) stably. Thermal conduction grease (SCH-20, Sanhayato) was applied between the atomizing electrode 105 and the cooling part 104.

The insulating part 305 was provided with the atomizing electrode 105. As the insulating part 305, a circular plate made of TEFLON (Registered Trade Mark) with a diameter of 10 millimeters and a thickness of 3 millimeters was employed. A concave structure with a diameter of 4 millimeter and a depth of 1 millimeter was provided at the center of the insulating part 305.

The intermediate electrode 106 was provided 3 millimeters away from the tip of the atomizing electrode 105. As the intermediate electrode 106, a circular ring made of stainless plate with an external diameter of 12 millimeters, an internal diameter of 8 millimeters, and a thickness of 0.5 millimeter was employed. The intermediate electrode 106 was fixed to the vessel 101 with a stainless anchor point. The intermediate electrode 106 was fixed to the portion made of a PEEK material of the vessel 101 to insulate the vessel 101 from the intermediate electrode 106 electrically.

The counter electrode 107 was provided at the above face of the vessel 101. As the counter electrode 107, a stainless needle was provided in the vessel 101. The length of the stainless needle was 3 millimeters. The diameter at the thickest portion of the stainless needle was 0.79 millimeter. The diameter at the thinnest portion of the stainless needle was 0.5 millimeter. The tip of the stainless needle was polished sharply to recover the chemical substance efficiently.

The second insulation part 307 was provided with the counter electrode 107. As the second insulation part 307, a circular plate made of Teflon (Registered Trade Mark) with a diameter of 10 millimeters and a thickness of 3 millimeters was employed. A concave structure with a diameter of 4 millimeters and a depth of 1 millimeter was provided at the center of the second insulation part 307.

The second cooling part 108 was provided at the end of the counter electrode 107. The contact area of the counter electrode 107 with the second cooling part 108 was 0.5 square millimeter. The second cooling part had a size of 14 millimeters×14 millimeters×1 millimeter. The second cooling part 108 had a maximum endotherm of 0.9 W and the largest temperature difference of 69 degree Celsius. The cooling surface of the second cooling part 108 was covered with a ceramic material. Since the ceramic material had a plurality of fine convexes and concaves on the surface thereof, the object which came in contact with the ceramic material was cooled efficiently.

The second heat radiation part 308 was provided with the second cooling part 108. Heat radiation fins were employed as the second heat radiation part 308. The second heat radiation part 308 was prepared with cutting work from the aluminum. The number of the heat radiation fins was six. Each of the heat radiation fins had a size of 16 millimeters×15 millimeters×1 millimeter. A cooling fan (KD1208PTBS2-6, SUNON) was provided in the neighborhood of the second heat radiation part 308 to promote heat radiation.

The second thermal protection part 309 was provided between the second cooling part 108 and the vessel 101. A rubber film with a thickness of 1 millimeter was employed as the second thermal protection part 309. A hole was provided at the portion of the rubber film to penetrate the atomizing electrode 105. The hole has a diameter of 1 millimeter.

Thermal conduction grease (SCH-20, Sanhayato) was applied between the counter electrode 107 and the second cooling part 108.

A valve 112a and a valve 112b were provided with the inlet 102 and the outlet 103, respectively. As the valve 112a and the valve 112b, ball valves were employed.

As the detecting electrode 109, an electrode obtained by printing carbon paste was used. The electrode had a size of 1.5 millimeters×1.5 millimeters. Two electrodes were provided on the support 110. As the support 110, polystyrene film was employed. The support 110 had a length of 25 millimeters and a width of 6 millimeters, and a thickness of 0.5 millimeter. The wire 402 was covered with plastic film not to come in contact with the second condensate liquid 206. The pad 403 was exposed.

The liquid detecting part 111 was formed by combining two types of LEDs. As the light-emitting part 111a, a white LED (NSPW500CS, Shinko-Denshi) was employed. As the light-receiving part 111b, a green LED (LP-5HGW4, LED PARADISE) was employed. The distance between the counter electrode 107 and the light-emitting part 111a was 3 millimeters. The distance between the counter electrode 107 and the light-receiving part 111b was 3 millimeters.

Next, the operating procedure of the analyzing device 100 is described below.

<Step (b)>

The gas sample 203 was injected from the inlet 102 into the vessel 101. As the gas sample 203, nitrogen gas containing volatile component of urine was used. The preparing method of the gas sample 203 is described below. First, one milliliter of urine collected from mice was filled in a vial container made of glass (Volume: 15 milliliters). An inlet for nitrogen gas and an outlet for gas sample were provided with the vial container. Nitrogen gas (degree of purity: 99.99%) was introduced from the inlet for nitrogen gas at a flowing rate of 500 sccm to spray to the urine. The nitrogen gas was passed through a bubbler filled with pure water of 100 milliliters to cause the nitrogen gas to contain a vapor. The gas sample 203 containing the volatile component of the urine was discharged from the gas outlet.

The injecting rate of the gas sample 203 into vessel 101 was 500 sccm.

Before the gas sample 203 was injected into the vessel 101, dry nitrogen gas was filled in the inside of the vessel 101.

Excess of the gas sample 203 was discharged through the outlet 103.

The inside of the vessel 101 had atmospheric pressure.

<Step (C)>

The atomizing electrode 105 was cooled to 2 degree Celsius by thermoelectric element.

After thermoelectric element start to be operated, the first condensate liquid 204 was formed on the outside surface of the atomizing electrode 105 in five seconds. At the initial stage of the forming, the first condensate liquid 204 was a liquid droplet with a diameter of not more than 10 micrometers. As time went by, the liquid droplet grew, and the entire surface of the atomizing electrode 105 was covered by the first condensate liquid 204.

<Step (d)>

The first condensate liquid 204 was configured to be a lot of electric-charged fine particles 205 with electrostatic atomization. At the initial stage of the electrostatic atomization, corona discharge may occur. The step (d) may be performed with the corona discharge.

The electric-charged fine particle 205 had a diameter of not less than 2 nm and not more than 30 nm. It is preferred that the electric-charged fine particle 205 exists solely one by one; however, two or more electric-charged fine particles 205 may be bound. In the present invention, the shape of the electric-charged fine particle 205 is not limited. The shape of the electric-charged fine particle 205 may be sphere, flat, or fusiform-shaped.

A direct current of 5 kV was applied between the atomizing electrode 105 and the intermediate electrode 106. The atomizing electrode 105 served as a cathode. The intermediate electrode 106 served as a GND electrode (ground electrode). When the atomizing electrode 105 was used as an anode and the intermediate electrode 106 was used as a GND electrode, identical effect was obtained. However, in this case, the step (d) was performed relatively-unstably.

A conical shape water column, which was called Taylor corn, was formed at the tip of the atomizing electrode 105. A lot of electric-charged fine particles 205 containing the chemical substance 202 were released from the tip of the Taylor corn.

The current flowing between the atomizing electrode 105 and the intermediate electrode 106 was monitored. When excess current flowed, the voltage application between the atomizing electrode 105 and the intermediate electrode 106 was interrupt, or the applied voltage was lowered.

<Step (e)>

The electric-charged fine particles 205 were recovered to the counter electrode 107 with electrostatic force. The voltage of +600 was applied to the counter electrode 107 with regard to the intermediate electrode 106. The step (e) was performed parallel to the step (b), the step (c), and the step (d). In light of the lifetime of the electric-charged fine particle 205, it is preferred that the step (e) is performed within ten minutes after the step (d) was begun.

The temperature of the counter electrode 107 was 2 degree Celsius. The electric-charged fine particles 205 were cooled and condensed to obtain the second condensate liquid 206. After the step (e) was begun, 1.0 microliter of the second condensate liquid 206 was obtained at the counter electrode 107 in one minute and forty seconds. The recovered electric-charged fine particles 205 may be frozen. The frozen electric-charged fine particles 205 may be thawed to obtain the second liquid condensate liquid 206.

<Step (f)>

The second condensate liquid 206 at the counter electrode 107 was detected with the liquid detecting part 111. A voltage of +3.0V was applied to the light-emitting part 111a. The voltage output from the light-receiving part 111b was measured with a digital voltmeter (ADVANTEST, TR6848).

Figure 23:
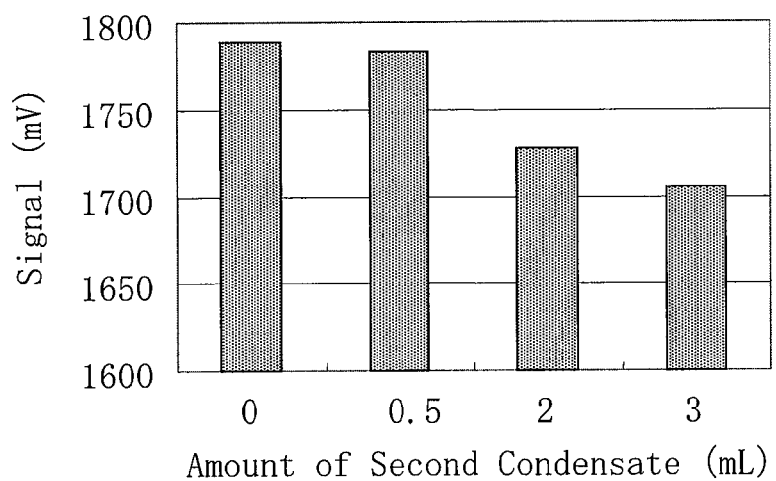
FIG. 23 shows a graph which illustrates the detecting result of the second condensate liquid in the example.

FIG. 23 shows the result of detection of the second condensate liquid 206 with the liquid detecting part 111. The vertical axis in the graph shown in FIG. 23 represents the voltage output from the light-receiving part 111b, namely a signal voltage. The signal voltage was decreased with the increase of the liquid amount of the second condensate liquid 206. FIG. 23 demonstrates that the liquid detecting part 111 achieved the detection of the second condensate liquid 206.

<Step (g)>

The detecting electrode 109 was moved manually at the position where it came in contact with the second condensate liquid 206. The detecting electrode 206 was moved straightly and horizontally.

Figure 24:
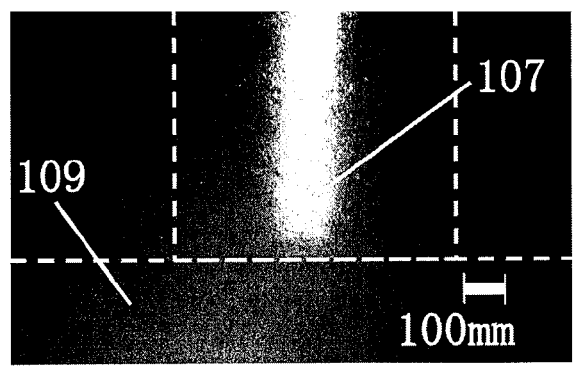
FIG. 24 shows a microscope photograph when the detecting electrode 109 was moved to the position where it became in contact with the second condensate liquid 206 in the movement step of the example.
Figure 25:
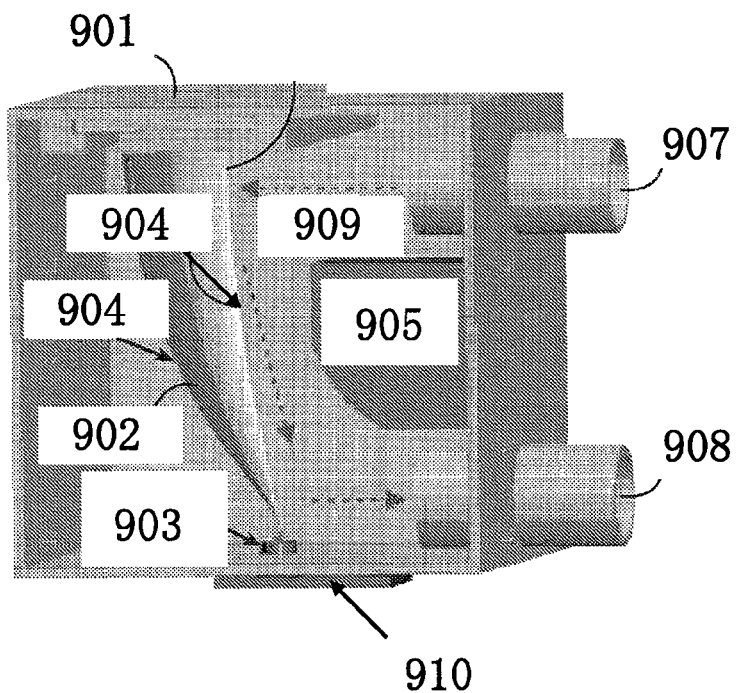
FIG. 25 shows an explanatory drawing of a prior analyzing device.
Figure 26:
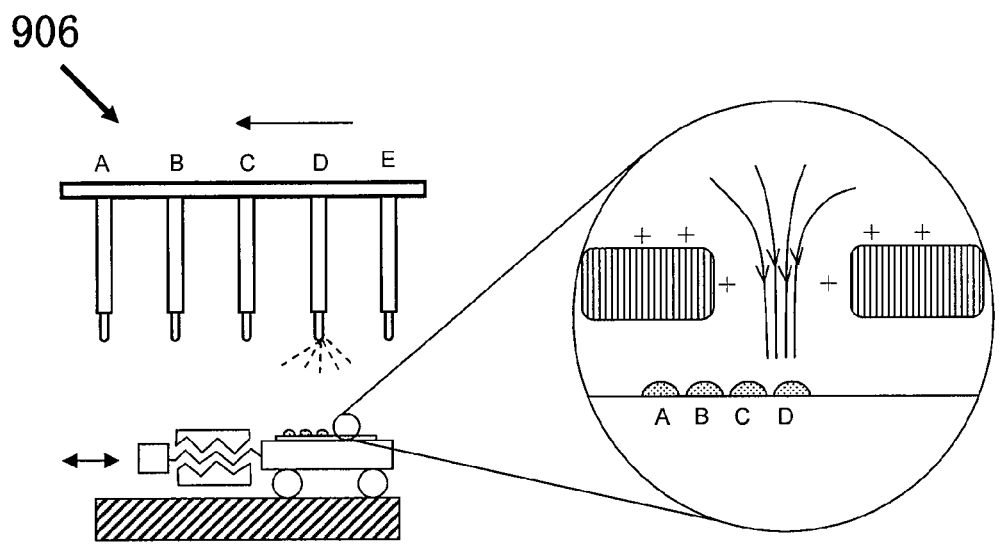
FIG. 26 shows an explanatory drawing of a prior electrostatic atomizing device.

FIG. 24 shows the microscope photograph when the detecting electrode 109 was moved to the position where it became in contact with the second condensate liquid 206. The present inventor observed how the detecting electrode 109 became in contact with the second condensate liquid 206 with a microscope (KEYENCE Company, VH-6300), and took a photograph. The second condensate liquid 206 was held between the counter electrode 107 and the detecting electrode 109. A direct voltage was applied in the condition where the second condensate liquid 206 is brought in contact with the counter electrode 107 and the detecting electrode 109.

The chemical substance 202 contained in the second condensate liquid 206 was detected with the detecting electrode 109. The change of the current value between the counter electrode 107 and the detecting electrode 109 was measured to detect the chemical substance 202 contained in the second condensate liquid 206. The temperature of the counter electrode 107 was room temperature (22 degree Celsius). The temperature of the counter electrode 107 could be increased by operating reversely the second cooling part 108, namely thermoelectric element to volatilize the second condensate liquid 206. The potentials of the counter electrode 107 and the detecting electrode 109 were fixed to be 0 V with regard to the intermediate electrode 106. The change of the electric resistance was measured with a digital voltmeter (ADVANTEST, TR6848). When the detecting electrode 109 was brought in contact with the second condensate liquid 206, the electric resistance between the counter electrode 107 and the detecting electrode 109 was decreased, compared to before they were brought in contact with each other.

From the foregoing description, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

INDUSTRIAL APPLICABILITY

The chemical substance analysis method of the present invention can be used for environmental field, food field, house field, automobile field, or security field. The chemical substance analysis method of the present invention can be used also for medical field or healthcare field such as a lifestyle-disease diagnosing device, a urine-diagnosing device, an exhalation-diagnosing device, or a stress-measuring device.

REFERENCE SIGNS LIST

100: Analyzing Device
101: Vessel
102: Inlet
103: Outlet
104: Cooling Part
105: Atomizing Electrode
106: Intermediate Electrode
107: Counter Electrode
108: Second Cooling Part 109, 109a, 109b: Detecting Electrode
110: Support
111: Liquid Detecting Part
111a: Light-emitting Part
111b: Light-receiving Part
112a, 112b: Valve
Water Vapor
202, 202a, 202b, 202c: Chemical Substance
203: Gas Sample
204: First Condensate Liquid
205: Electric-charged Fine Particle
206: Second Condensate Liquid
301a, 301b: Electric Liquid Detecting Part
303: Hear Radiation Part
304: Thermal Protection Part
305: Insulating Part
307: Second Insulation Part
308: Second Heat Radiation Part
309: Second Thermal Protection Part
401: Through-hole
407: Rotation Center
408: Counter Electrode
901: Exhalation Analyzing Device
902: Condensate Part
903: Recover Well
904: Curvature
905: Flow Path Structure
906: Electrostatic Atomizing Device
907: Inlet
908: Outlet
909: Gas Flow
910: Sampling Strip

The invention claimed is:

1. A method for detecting a chemical substance contained in a gas sample using an analyzing device, comprising the following steps (a) to (h):
   a step (a) of preparing the analyzing device, wherein, the analyzing device comprises:
      a vessel,
      an inlet for injecting the gas sample, and provided with the vessel,
      an atomizing electrode inside the vessel,
      a cooling part cooling the atomizing electrode,
      a counter electrode provided in the vessel,
      an intermediate electrode disposed between the atomizing electrode and the counter electrode, and
      a liquid detector,
   a step (b) of injecting the gas sample from the inlet to the vessel, wherein
      the gas sample contains vapor,
   a step (c) of cooling the atomizing electrode with the cooling part to condense the gas sample into a first condensate liquid on the surface of the atomizing electrode,
   a step (d) of applying a potential difference between the atomizing electrode and the intermediate electrode to cause the first condensate liquid to be electric-charged fine particles,
   a step (e) of recovering the electric-charged fine particles on the surface of the counter electrode by applying a potential difference between the intermediate electrode and the counter electrode to obtain a second condensate liquid,
   a step (f) of detecting with the liquid detector that the second condensate liquid has not less than predetermined amount,
   a step (g) of inserting a support comprising a detecting electrode into the vessel to bring the detecting electrode into contact with the second condensate liquid, and
   a step (h) of applying current voltage between the counter electrode and the detecting electrode to detect the chemical substance on the basis of the value of the generated current.

2. A method according to claim 1, wherein the analyzing device comprises a second cooling part cooling the counter electrode, wherein the counter electrode is cooled by the second cooling part to no higher than the dew-point temperature of water vapor in the step (e).

3. A method according to claim 1, wherein the step (e) is stopped when it is detected that the second condensate liquid has not less than the predetermined amount in the step (f).

4. A method according to claim 1, wherein the step (g) and the step (h) are performed after the step (e) is stopped.

5. A method according to claim 1, wherein the potential of the counter electrode is equal to the potential of the detecting electrode in the step (h).

* * * * *